United States Patent [19]

Bissolino et al.

[11] Patent Number: 5,077,286
[45] Date of Patent: Dec. 31, 1991

[54] BETA-LACTAM DERIVATIVES OF THE 4-ACYLCEPHEM SULPHONE AND 3-ACYLPENAM SULPHONE-TYPE

[75] Inventors: Pierluigi Bissolino, S.Giorgio Lomellina; Marco Alpegiani, Milan; Ettore Perrone, Boffalora Ticino; Piergiuseppe Orezzi, Milan; Giuseppe Cassinelli, Voghera; Giovanni Franceschi, Milan, all of Italy

[73] Assignee: Farmitalia Carlo Erba S.r.l., Milan, Italy

[21] Appl. No.: 335,824

[22] Filed: Apr. 10, 1989

[30] Foreign Application Priority Data

Apr. 13, 1988 [GB] United Kingdom ............. 8808701

[51] Int. Cl.$^5$ .............. C07D 501/20; A61K 31/545
[52] U.S. Cl. ............................. 514/201; 514/202; 514/203; 514/204; 540/221; 540/222; 540/225; 540/227; 540/230
[58] Field of Search ............ 514/201, 202, 204, 203; 540/222, 221, 227, 225

[56] References Cited

U.S. PATENT DOCUMENTS 4,547,371 10/1985 Doherty et al. ............. 540/215
4,637,999 1/1987 Doherty et al. ............. 540/226

FOREIGN PATENT DOCUMENTS 187476 8/1982 New Zealand.
190797 8/1982 New Zealand.
193020 11/1982 New Zealand.
193713 5/1984 New Zealand.
200067 7/1985 New Zealand.
200066 8/1985 New Zealand.
208379 5/1987 New Zealand.

OTHER PUBLICATIONS

"Enclosure 1" (10 pages) Reference: HLE Role, etc.

Primary Examiner—Nicholas S. Rizzo
Attorney, Agent, or Firm—Oblon, Spivak, McClelland, Maier & Neustadt

[57] ABSTRACT

Compounds of formulae Ia and Ib

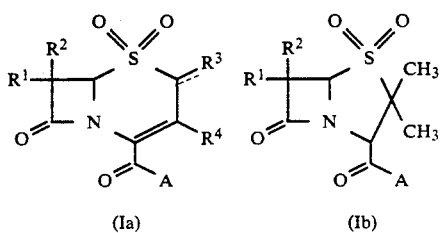

wherein A is hydrogen atom or an organic residue, $R^1$ is halogen atom, or an organic group, $R^2$ is hydrogen or halogen atom, $C_1$-$C_4$ alkyl or alkoxy group, $R^3$ is hydrogen atom, $C_1$-$C_4$ alkyl or alkoxy group, benzyl or a methylene group and $R_4$ is an organic residue are disclosed. Compounds (Ia) and (Ib) are endowed with elastase inhibitory activity. A two-step process for their preparation starting from the corresponding 4-carboxy cephem or 3-carboxy penam is also provided.

8 Claims, No Drawings

BETA-LACTAM DERIVATIVES OF THE 4-ACYLCEPHEM SULPHONE AND 3-ACYLPENAM SULPHONE-TYPE

BACKGROUND OF THE INVENTION

Field of the Invention

The present invention relates to 4-acylcephem sulphones and 3-acylpenam sulphones, their preparation and to pharmaceutical and veterinary compositions containing them.

SUMMARY OF THE INVENTION

The invention provides 4-acylcephem sulphones and 3-acylpenam sulphones of formula (Ia) and (Ib) respectively and their pharmaceutically and veterinarily acceptable salts;

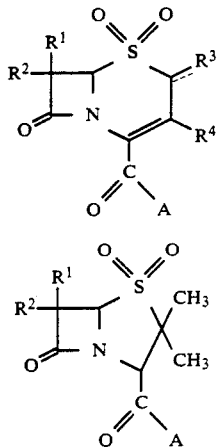

In these formulae (Ia) and (Ib), A represents a hydrogen atom or an organic radical selected from $C_1$-$C_{12}$ straight or branched alkyl; $C_2$-C10 alkenyl; $C_2$-$C_{10}$ alkynyl; $C_6$-$C_{10}$ aryl; $C_3$-$C_8$ cycloalkyl; $C_5$-$C_8$ cycloalkenyl; aralkyl, aralkenyl, aralkynyl or (cycloalkyl)alkyl wherein the aryl, cycloalkyl, alkyl, alkenyl and alkynyl moieties are as defined above; a 5- or 6-membered, saturated or unsaturated, heterocyclyl ring, containing at least one heteroatom chosen from O, S and N, which is optionally fused to a second 5- or 6-membered heterocyclyl group or to a $C_3$-$C_8$ cycloalkyl group; or heterocyclyalkyl, heterocyclyalkenyl or heterocyclyalkynyl wherein the heterocyclyl, alkyl, alkenyl and alkynyl groups are as defined above.

Each of the organic radical is unsubstituted or substituted by at least one substituent selected from halo (i.e., fluoro, chloro, bromo or iodo); hydroxy; nitro; azido; diazo; amino (i.e., —$NH_2$, or —NHR' or —NR'R'') wherein R' and R'', which are the same or different, are $C_1$-$C_7$ straight or branched alkyl, phenyl or benzyl; formyl (i.e., —CHO); mercapto (i.e., —SH or SR') wherein R' is as defined above; cyano; carboxy (alkyl) (i.e., $(CH_2)_tCO_2H$ or $(CH_2)_tCO_2R'$) wherein R' is as defined above and t is 0, 1, 2 or 3; sulpho (i.e., —$SO_3H$); acyl (i.e., —C(O)R') wherein R' is as defined above or trifluoroacetyl (i.e., —C(O)$CF_3$) ; carbamoyl (i.e., —$CONH_2$); N-methylcarbamoyl (i.e., —$CONHCH_3$) or N-(carboxymethyl)carbamoyl (i.e., —CONH—$CH_2CO_2H$); carbamoyloxy (i.e., —$OCONH_2$); acyloxy (i.e., —OC(O)R') wherein R' is as defined above or formyloxy (i.e., —OC(O)H); alkoxycarbonyl or benzyloxycarbonyl (i.e., —C(O)OR') wherein R' is as defined above: alkoxycarbonyloxy or benzyloxycarbonyloxy (i.e., —OC(O)R') wherein R' is as defined above; alkoxy, phenoxy or benzyloxy (i.e., —O—R') wherein R' is as defined above; alkylthio, phenylthio or benzylthio (i.e., —S—R') wherein R' is as defined above; alkylsulphinyl, phenylsulphinyl or benzylsulphinyl (i.e., —S(O)R') wherein R' is as defined above; alkylsulphonyl, phenylsulphonyl or benzylsulphonyl (i.e., S(O)$_2$R') wherein R' is as defined above; acylamino (i.e., —NHC(O)R''' or —NHC(O)OR''') wherein R''' is $C_1$-$C_7$ straight or branched alkyl, phenyl, benzyl, $CH_2CH_2CO_2H$ or $CH_2CH_2CH_2CO_2H$; sulphonamido (i.e., —NH—$SO_2R'$) wherein R' is as defined above; guanidino (i.e., —NHC(=NH)$NH_2$); $C_1$-$C_4$ alkyl, $C_2$-$C_4$ alkenyl or alkynyl; $C_3$-$C_6$ cycloalkyl; and substituted methyl selected from chloromethyl, fluoromethyl, difluoromethyl, trifluoromethyl, aminomethyl, azidomethyl, cyanomethyl, carboxymethyl, carbamoylmethyl, carbamoyloxymethyl, hydroxymethyl, $C_3$-$C_4$ alkoxycarbonylmethyl, guanidinomethyl.

$R^1$ represents:
(1) chloro, fluoro, bromo or iodo;
(2) A as defined above;
(3) an ether group of the formula —O—A wherein A is as defined above;
(4) a thioether, sulphoxide or sulphone (i.e., —S(O)$_n$A wherein n is either 0, 1 or 2 and wherein A is as defined above);
(5) acyloxy (i.e., —OC(O)A wherein A is as defined above);
(6) sulphonyloxy (i.e., —O—$SO_2$A wherein A is as defined above); or
(7) acylamino (i.e., —NHC(O)A wherein A is as defined above) or acylamino (i.e., —NH—Z wherein Z is a mono, di- or tripeptide composed of D or L α-aminoacids chosen from Ala, Gly, Val, Leu, Ile, Phe and Pro, and with the terminal amino group either free, or acylated by a group —C(O)R''' or —C(O)OR''' wherein R''' is as defined above).

$R^2$ is either hydrogen or:
(1) $C_1$-$C_4$ alkyl;
(2) $C_1$-$C_4$ alkanoyloxy; or
(3) chloro bromo or fluoro.

$R^3$ is either hydrogen or:
(1) $C_1$-$C_4$ alkyl;
(2) $C_1$-$C_4$ alkoxy;
(3) benzyl;
(4) halo; or
(5) a methylene group (i.e., =$CH_2$) or a group of the formula =$CHR^{IV}$, wherein $R^{IV}$ is either $C_1$-$C_4$ alkyl, phenyl, carboxy, or $C_1$-$C_4$ alkoxycarbonyl.

$R^4$ represents:
(1) A as defined above;
(2) chloro or fluoro;
(3) an oxy group (i.e., —O—A, wherein A is as defined above);
(4) a sulphenyl, sulphinyl or sulphonyl group (i.e., —S(O)$_n$A, wherein n and A are as defined above);
(5) an acyl group (i.e., —C(O)A, —C(O)OA or —$CO_2$H wherein A is as defined above);
(6) an oxymethyl group (i.e., —$CH_2$—O—A wherein A is as defined above);
(7) a thiomethyl group or a derivative thereof of the formula —$CH_2S(O)_n$A wherein n and A are as defined above;

(8) an acyloxymethyl group (i.e., —CH$_2$OC(O)A or —CH$_2$—O—Z, wherein A and Z are as defined above);

(9) an acylthiomethyl group (i.e., —CH$_2$SC(O)A wherein A is as defined above);

(10) an aminomethyl group (i.e., —CH$_2$—N(A)A' wherein A is as defined above and A', being the same or different, is as defined for A; or A and A' taken together with the nitrogen atom to which they are attached represent a heterocyclic ring);

(11) an ammoniomethyl group of the formula

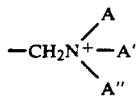

wherein A and A' are as defined above and A'', being the same or different, is as defined for A; or A is alkyl and A' and A'' together with the nitrogen atom to which they are attached represent a heterocyclic ring; or A, A' and A'' together with the nitrogen atom to which they are attached represent an aromatic heterocyclic ring; or

(12) acylaminomethyl (i.e., —CH$_2$NH—C(O)A or —CH$_2$—NH—Z wherein A and Z are as defined above).

The present invention also provides the salts of those compounds of formulae (Ia) and (Ib) that have salt-forming groups, especially the salts of the compounds having a carboxylic group, a basic group (e.g. an amino or guanidino group), or a quaternary ammonium group. The preferred salts are the physiologically tolerable salts. For example, these include alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic organic acids (e.g. acetic, trifluoroacetic, p-toluenesulphonic acid) Some compounds of formula (Ia) or (Ib) which contain a carboxylate and an ammonium group may exist as zwitterions. Such salts are also part of the present invention.

DETAILED DESCRIPTION OF THE PREFERRED EMBODIMENTS

In the present invention, the definition C$_3$-C$_8$ cycloalkyl includes cyclopropyl, cyclobutyl, cyclopentyl, cyclohexyl, cycloheptyl, and cyclooctyl groups. The definition C$_5$-C$_8$ cycloalkenyl includes cyclopentenyl and cyclohexenyl group.

The definition heterocyclyl ring includes thiazolyl, triazolyl, thiadiazolyl, tetrazolyl, triazinyl, pyrrolyl, imidazolyl, furyl, thienyl, morpholinyl, pyranyl, pyridyl, pyrimidinyl, pyrazinyl, pyridazinyl and thiopyranyl residues.

The present invention encompasses all the possible stereoisomers, as well as their racemic or optically active mixtures. However, the configurations depicted in formulae (Ia') and (Ib') are particularly preferred:

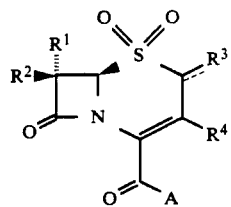

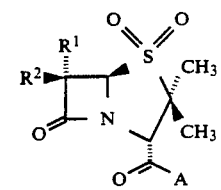

In formulae (Ia') and (Ib'), A is a C$_1$-C$_{10}$ straight or branched alkyl, alkenyl, or alkynyl; C$_3$-C$_8$ cycloalkyl; dimethylphenyl, diphenylmethyl, phenyl or benzyl. These alkyl, phenyl and benzyl groups are either unsubstituted or substituted by fluoro, chloro, carboxy, C$_1$-C$_4$ alkoxycarbonyl, carbamoyl, carbamoyloxy, methylsulphonyl, diazo, hydroxy, methoxy, ethoxy, tert-butoxy, benzyloxy, acetoxy, pivaloyloxy, benzoxy and phenylacetoxy.

R$^1$ is (1') chloro, fluoro or bromo, (2') C$_1$-C$_4$ alkyl, 1-(hydroxy)ethyl, 1-(benzyloxy)ethyl, 1-(benzyloxycarbonyloxy)ethyl, 1-(phenylacetoxy)ethyl, 2-fluoro-1-hydroxyethyl, isopropyl, phenyl or benzyl;

(3') methoxy, ethoxy, isopropoxy, phenoxy or benzyloxy;

(4') methylthio;

(5') formyloxy, acetoxy or phenylacetoxy;

(6') mesyloxy or tosyloxy;

(7') formamido, acetamido, fluoroacetamido, trifluoroacetamido or chloroacetamido;

(8') R$^v$-Ala-NH, wherein R$^v$ is either acetyl, tert-butoxycarbonyl, benzoxycarbonyl or HOOC—CH$_2$CH$_2$-C(O)—;

(9') R$^v$-Val-NH wherein R$^v$ is as defined above; or (10') Val-Pro-NH, Lys-NH, Ala-Ala-Pro-NH, wherein the terminal amino group of Val, Lys or Ala respectively or the α-amino group of Lys is either free or acylated with a group R$^v$ as defined above.

R$^2$ is hydrogen, chloro or fluoro.

R$^3$ is hydrogen, methyl, benzyl, or bromo.

R$^4$ is either hydrogen or (1') methyl, chloromethyl, bromomethyl or benzyl;

(2') chloro;

(3') methoxy or benzyloxy;

(4') methylthio;

(5') formyl, acetyl, benzoyl, carboxy, methoxycarbonyl, ethoxycarbonyl, tert-butoxycarbonyl or benzyloxycarbonyl;

(6') methoxymethyl, ethoxymethyl, isopropoxymethyl; or benzyloxymethyl, phenoxymethyl, 3-pyridyloxymethyl wherein the phenyl and pyridyl rings are either unsubstituted or substituted by one group or two equal or different groups chosen from hydroxy, carboxy, amino and C$_1$-C$_4$ alkoxycarbonyl;

(7') methylthiomethyl, phenylthiomethyl, methylsulphonylmethyl, phenylsulphynylmethyl, phenylsulphonylmethyl or a group —CH$_2$—S—CH$_2$—CH(NH$_2$)CO$_2$H wherein the amino group is either free or protected with tert-butoxycarbonyl or benzoxycarbonyl, acetyl and the carboxy group is either free or as the ethyl, tert-butyl, benzyl, methyl or diphenylmethyl ester;

(8') —CH₂-S-Het wherein Het is a heterocyclic ring, preferably chosen from:

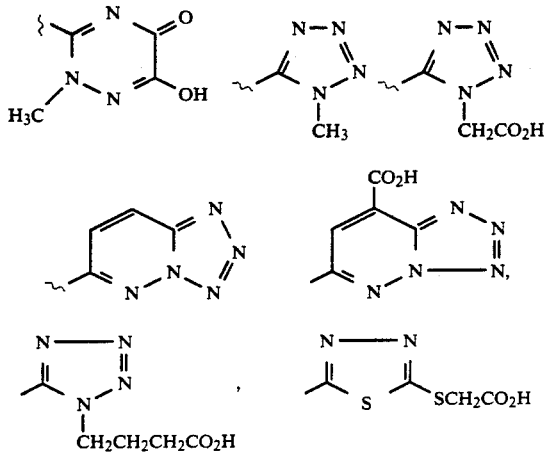

(9') acetoxymethyl, benzoxymethyl, phenyloacetoxymethyl or $C_3$-$C_{10}$ alkanoyloxymethyl wherein the above groups are either unsubstituted or substituted by one group or two equal or different groups selected from carboxy, hydroxy and amino wherein the amino may be free or acylated with a group selected from acetyl (Ac), benzoxycarbonyl (Cbz), tert-butoxycarbonyl (Boc), succinyl (i.e., HOOCCH₂CH₂CO—) and glutaryl (i.e., HOOC—CH₂—CH₂—CH₂—CO—);

(10') a group Z—OCH₂— wherein Z is Val-Pro, Ac-Val-Pro, Cbz-Val-Pro or Boc-Val-Pro;

(11') acetylthiomethyl;

(12') aminomethyl or $C_1$-$C_4$ alkylaminomethyl wherein the alkyl is either unsubstituted or substituted by a carboxy group; in particular —CH₂-Ala, —CH₂-Gly or —CH₂-Val;

(13') trialkylammoniomethyl wherein the alkyl group is chosen from methyl, ethyl, propyl or butyl, optionally substituted by a carboxy group;

alkyl(cycloalkyl)ammoniomethyl selected from the following group:

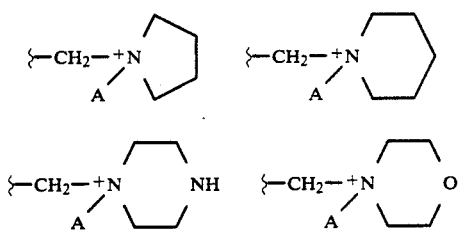

wherein A is as defined above;
pyridiniomethyl

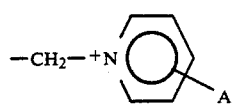

wherein A is as defined above;
4-carbamoylpyridiniomethyl; or quinuclidiniomethyl optionally substituted by a carbamoyl group or by a group A as defined above; or (14') acetylaminomethyl, benzoylaminomethyl; or Ala-NH-CH₂—, Gly-NH-CH₂—, Val-NH-CH₂—, Pro-NH-CH₂—, Phe-NH-CH₂— wherein the terminal amino of Ala, Gly, Val, Pro, Phe is either free or acylated with a group selected from Ac, Cbz, Boc, succinyl and glutaryl; or Z-NH-CH₂ wherein Z represents Val-Pro, Ala-Ala or Ala-Pro and wherein the terminal amino group of Val and Ala is either free or acylated with a group selected from Ac, Cbz, Boc, succinyl and glutaryl;

and the pharmaceutically and veterinarily acceptable salts thereof.

Still more preferred are compounds of formulae (Ia″) and (Ib″):

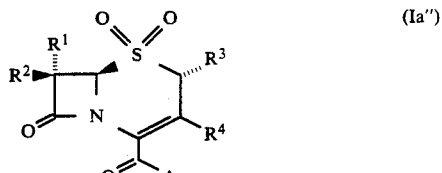 (Ia″)

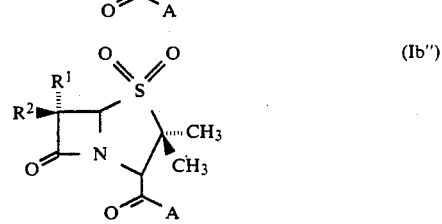 (Ib″)

In formulae (Ia″) and (Ib″), A is selected from hydrogen, methyl, ethyl, tert-butyl, neo-pentyl, phenyl, benzyl, 1-phenylethyl, dimethylphenyl, diphenylmethyl, propenyl, phenylethinyl, cyclopentyl, 1-carboxycyclopentyl, diazomethyl, chloromethyl, hydroxymethyl, methoxymethyl, acetoxymethyl and pivaloyloxymethyl.

$R^1$ is chloro, bromo, fluoro, methoxy, formamido, acetamido, trifluoroacetamido, methyl, ethyl, 1-(hydroxy)ethyl, (1-benzyloxycarbonyloxy)ethyl, (1-benzoyloxy)ethyl, 1-(phenylacetoxy)ethyl, or Ala-NH, Acetyl-Ala-NH, succinyl-Val-NH, L-Val-L-Pro-NH, succinyl-Lys-NH, Ala-Ala-Pro-NH or acetyl-Ala-Ala-Pro-NH.

$R^2$ is hydrogen.

$R^3$ is hydrogen, methyl, or bromo.

$R^4$ is methyl, bromomethyl, acetoxymethyl, hydroxymethyl, carbamoyloxymethyl, methoxymethyl, carboxy, phenoxymethyl, aminomethyl, pyridiniomethyl or a group selected from:

(1) —CH₂OCONH—CH₂CO₂H;
(2) —CH₂OCONH—CH($R^{VI}$)CO₂H wherein $R^{VI}$ is phenyl or $C_1$-$C_7$ straight or branched alkyl;
(3) —CH₂OC(O)CH₂CH₂CO₂H;
(4) —CH₂OC(O)—(p-$C_6H_4$)—CO₂H or —CH₂OC(O)—(p-$C_6H_4$)—CO₂ $^tC_4H_9$;
(5)

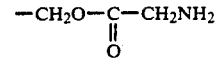

or its N-Ac, N-Boc or N-CbZ derivative;

(6) 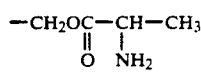

or its N-Ac, N-Boc or N-CbZ derivative;

(7) 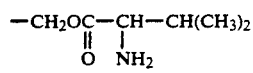

or its N-Ac, N-Boc or N-CbZ derivative;

(8) 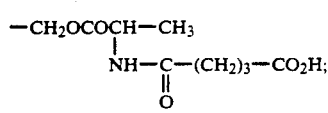

(9) 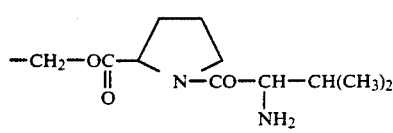

of its N-Ac, N-Boc or N-Cbz derivative;

(10) 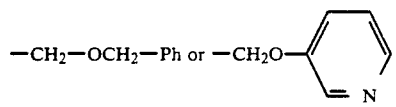

(11) 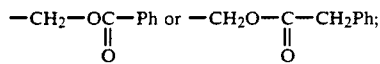

(12) —CH$_2$SO$_2$CH$_3$ or —CH$_2$—S(O)Ph;

(13) 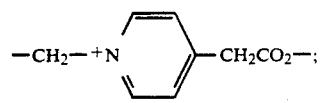

(14) 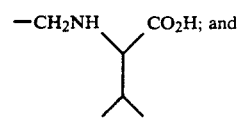

(15) 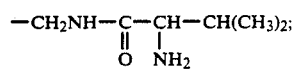

(16) —CH$_2$S-Het, wherein Het is a heterocyclic ring, preferably chosen from:

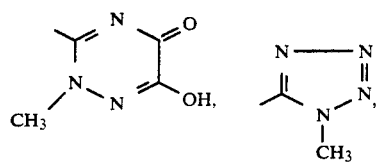

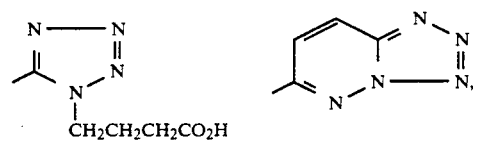

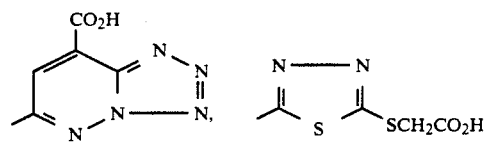

and the pharmaceutically and veterinarily acceptable salts thereof.

Specific examples of the preferred compounds of the present invention are those listed herein below:

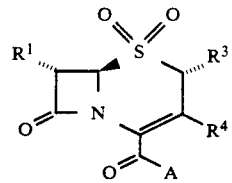

| no | A | R$^1$ | R$^3$ | R$^4$ |
|----|---|-------|-------|-------|
| 1 | $^tC_4H_9$ | Cl | H | CH$_3$ |
| 2 | " | " | " | CH$_2$Br |
| 3 | " | " | " | CH$_2$OCOCH$_3$ |
| 4 | " | " | " | CH$_2$OH |
| 5 | " | " | " | CH$_2$OCONH$_2$ |
| 6 | " | " | " | CH$_2$OCH$_3$ |
| 7 | " | " | " | CH$_2$O—Ph |
| 8 | " | " | " | CH$_2$NH$_2$ |
| 9 | " | " | " | CH$_2$$^+$N(C$_5$H$_5$)·Cl$^-$ |
| 10 | " | " | " | CH$_2$OCONH—CH$_2$CO$_2$H |
| 11 | $^tC_4H_9$ | Cl | H | CH$_2$OCOCH$_2$CH$_2$CO$_2$H |
| 12 | " | " | " | CH$_2$OCOPh |

-continued

| # | | | | |
|---|---|---|---|---|
| 13 | " | " | " | CH₂OC(=O)-C₆H₄-CO₂H (para) |
| 14 | " | " | " | CH₂OCOCH₂—Ph |
| 15 | " | " | " | CH₂S—Ph |
| 16 | " | " | " | CH₂O-(3-pyridyl) |
| 17 | $^tC_4H_9$ | Cl | H | CH₂OC(=O)CH₂NH₂ |
| 18 | " | " | " | CH₂OC(=O)CH₂NH—C(=O)—O$^tC_4H_9$ |
| 19 | " | " | " | CH₂OC(=O)-C₆H₄-CO₂$^tC_4H_9$ (para) |
| 20 | " | " | " | CH₂OC(=O)—CH(NH₂)—CH(CH₃)₂ |
| 21 | " | " | " | CH₂OC(=O)—CH(NHCOO$^tC_4H_9$)—CH(CH₃)₂ |
| 22 | " | " | " | CH₂OC(=O)—CH(NH₂)—CH₃ |
| 23 | " | " | " | CH₂OC(=O)—CH(NHC(=O)O$^tC_4H_9$)—CH₃ |
| 24 | " | " | " | CH₂OC(=O)—CH(NH₂)—CH₂CO₂H |
| 25 | " | " | " | CH₂OC(=O)—CH(CH₃)—NH—C(=O)—(CH₂)₃—CO₂H |
| 26 | " | " | " | CH₂OC(=O)-[N-pyrrolidinyl-C(=O)—CH(NH₂)—CH(CH₃)₂] |

-continued

| # | R1 | R2 | R3 | R4 |
|---|---|---|---|---|
| 27 | $^tC_4H_9$ | Cl | H | pyrrolidine-CH₂OC(=O)- attached via N to C(=O)CH(CH(CH₃)₂)NH-COO-$^tC_4H_9$ |
| 28 | " | " | " | $CH_2SO_2CH_3$ |
| 29 | " | " | " | $CH_2S(=O)Ph$ |
| 30 | " | " | " | $CH_2{-}^+N{-}pyridinium{-}CH_2CO_2^-$ |
| 31 | " | " | " | $CH_2NHCH(CH(CH_3)_2)CO_2H$ (valine-like) |
| 32 | " | " | " | $CH_2NH{-}C(=O){-}CH(NH_2)CH(CH_3)_2$ |
| 33 | $C_2H_5$ | Cl | H | $CH_3$ |
| 34 | " | " | " | $CH_2OCOCH_3$ |
| 35 | $CH_2Ph$ | " | " | $CH_2OCOCH_3$ |
| 36 | " | " | " | $CH_2OCONHCH_2CO_2H$ |
| 37 | $CH_2{}^tC_4H_9$ | " | " | $CH_2OCOCH_3$ |
| 38 | Ph | " | " | " |
| 39 | H | " | " | " |
| 40 | $CH_2OCOCH_3$ | Cl | H | $CH_2OCOCH_3$ |
| 41 | $CH_2OCH_3$ | " | " | " |
| 42 | $CH(CH_3)Ph$ | " | " | " |
| 43 | $CH_2Cl$ | " | " | " |
| 44 | $CH_2N_2$ | " | " | " |
| 45 | $CH_3$ | " | " | " |
| 46 | $CH_2I$ | " | " | " |
| 47 | $CH_2OH$ | " | " | " |
| 48 | $CH_2OPh$ | " | " | " |
| 49 | $^tC_4H_9$ | $OCH_3$ | H | $CH_3$ |
| 50 | " | " | " | $CH_2Br$ |
| 51 | " | " | " | $CH_2OCOCH_3$ |
| 52 | " | " | " | $CH_2OH$ |
| 53 | " | " | " | $CH_2OCONH_2$ |
| 54 | " | " | " | $CH_2OCH_3$ |
| 55 | " | " | " | $CH_2O{-}Ph$ |
| 56 | " | " | " | $CH_2NH_2$ |
| 57 | " | " | " | $CH_2{-}^+N{-}pyridinium \cdot Cl^-$ |
| 58 | " | " | " | $CH_2OCONH{-}CH_2CO_2H$ |
| 59 | " | " | " | $CH_2OCOCH_2CH_2CO_2H$ |
| 60 | " | " | " | $CH_2OCOPh$ |
| 61 | $^tC_4H_9$ | $OCH_3$ | H | $CH_2OCO{-}C_6H_4{-}CO_2H$ (para) |
| 62 | " | " | " | $CH_2OCOCH_2Ph$ |
| 63 | " | " | " | $CH_2S{-}Ph$ |
| 64 | " | " | " | $CH_2SO_2CH_3$ |
| 65 | " | " | " | $CH_2S(=O)Ph$ |

-continued

| # | | | | |
|---|---|---|---|---|
| 66 | " | " | " | −CH$_2^+$N(pyridinium)−CH$_2$CO$_2^-$ |
| 67 | " | " | " | −CH$_2$NH−CH(CO$_2$H)−CH(CH$_3$)$_2$ |
| 68 | " | " | " | CH$_2$O−(3-pyridyl) |
| 69 | " | " | " | CH$_2$OCOCH$_2$NH$_2$ |
| 70 | " | " | " | CH$_2$OCOCH$_2$NHCOO$^t$C$_4$H$_9$ |
| 71 | " | " | " | CH$_2$OCO−C$_6$H$_4$−CO$_2{}^t$C$_4$H$_9$ |
| 72 | " | " | " | CH$_2$OC(O)−CH(NH$_2$)−CH(CH$_3$)$_2$ |
| 73 | " | " | " | CH$_2$OC(O)−CH(NHC(O)O$^t$C$_4$H$_9$)−CH(CH$_3$)$_2$ |
| 74 | " | " | " | CH$_2$OC(O)−CH(NH$_2$)−CH$_3$ |
| 75 | $^t$C$_4$H$_9$ | OCH$_3$ | H | CH$_2$OC(O)−CH(CH$_3$)−NHC(O)O$^t$C$_4$H$_9$ |
| 76 | " | " | " | CH$_2$OC(O)−CH(NH$_2$)−CH$_2$CO$_2$H |
| 77 | " | " | " | CH$_2$OC(O)−CH(CH$_3$)−NH−C(O)−(CH$_2$)$_3$−CO$_2$H |
| 78 | " | " | " | CH$_2$OC(O)−(prolinyl N-COCH(NH$_2$)CH(CH$_3$)$_2$) |
| 79 | " | " | " | CH$_2$OC(O)−(prolinyl N-COCH(CH(CH$_3$)$_2$)NHCO$_2{}^t$C$_4$H$_9$) |

-continued

| # | Col2 | Col3 | Col4 | Col5 |
|---|---|---|---|---|
| 80 | " | " | " | CH₂SCH₂CH(CO₂CHPh₂)(NHCO₂ᵗC₄H₉) |
| 81 | " | " | " | CH₂SCH₂CH(CO₂H)NHCO₂ᵗC₄H₉ |
| 82 | " | " | " | CH₂SCH₂CH(CO₂H)NH₂ |
| 83 | " | " | " | CH₂NH—C(=O)—CH(NH₂)CH(CH₃)₂ |
| 84 | C₂H₅ | " | " | CH₂SOPh |
| 85 | " | " | " | CH₂OCOCH₃ |
| 86 | CH₂Ph | OCH₃ | H | CH₂SOPh |
| 87 | " | " | " | CH₂OCOCH₃ |
| 88 | CH₂ᵗC₄H₉ | " | " | " |
| 89 | Ph | " | " | " |
| 90 | H | " | " | " |
| 91 | CH₃ | " | " | " |
| 92 | CH₂OCH₃ | " | " | " |
| 93 | CH₂OPh | " | " | " |
| 94 | CH₂Cl | " | " | " |
| 95 | ᵗC₄H₉ | F | " | " |
| 96 | " | NHCHO | " | " |
| 97 | " | NHCOCH₃ | " | " |
| 98 | " | NHCOCF₃ | " | " |
| 99 | " | CH₃ | " | " |
| 100 | " | C₂H₅ | " | " |
| 101 | " | CH(OH)CH₃ | " | " |
| 102 | ᵗC₄H₉ | CH(OCOCH₂Ph)CH₃ | H | CH₂OCOCH₃ |
| 103 | " | NH—C(=O)—CH(NHCOCH₃)(CH₃) | " | " |
| 104 | " | NH—C(=O)—CH(NH₂)(CH₃) | " | " |
| 105 | " | NH—C(=O)—CH(CH(CH₃)₂)(NHC(CH)₂CO₂H) | " | " |
| 106 | " | NH—C(=O)—[pyrrolidine with NCOCHNH₂-CH(CH₃)₂] | " | " |
| 107 | " | NH—C(=O)—CH((CH₂)₄—NH₂)(NHCO—CH₂CH₂CO₂H) | " | " |

-continued
| no | | | | | |
|---|---|---|---|---|---|
| 108 | " | 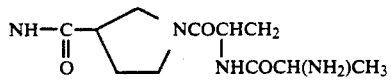 | | " | " |
| 109 | " | 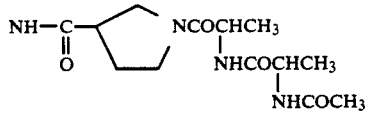 | | " | " |
| 110 | $^tC_4H_9$ | Cl | | $CH_3$ | $CH_2OCOCH_3$ |
| 111 | $CH_2Cl$ | Cl | | " | " |
| 112 | $^tC_4H_9$ | $OCH_3$ | | " | " |
| 113 | $CH_2F$ | " | | " | " |
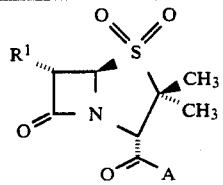
| no | A | $R^1$ |
|---|---|---|
| 114 | $CH_2Ph$ | Cl |
| 115 | $CH_3$ | " |
| 116 | $C_2H_5$ | " |
| 117 | $^tC_4H_9$ | " |
| 118 | H | " |
| 119 | Ph | " |
| 120 | $CH_2N_2$ | " |
| 121 | $CH_2Cl$ | " |
| 122 | $CH_2Ph$ | $OCH_3$ |
| 123 | $CH_3$ | " |
| 124 | $C_2H_5$ | " |
| 125 | $^tC_4H_9$ | " |
| 126 | H | " |
| 127 | Ph | $OCH_3$ |
| 128 | $CH_2OPh$ | " |
| 129 | $CH_2Cl$ | " |
| 130 | $^tC_4H_9$ | F |
| 131 | " | NHCHO |
| 132 | " | NHCOCH$_3$ |
| 133 | " | NHCOCF$_3$ |
| 134 | " | $CH_3$ |
| 135 | " | $C_2H_5$ |
| 136 | " |  |
| 137 | " | 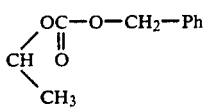 |
| 138 | " | 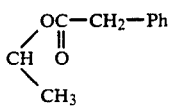 |
| 139 | $^tC_4H_9$ | 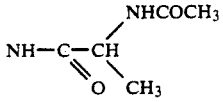 |

-continued
| 140 | " | 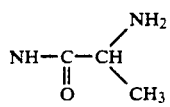 |
| 141 | " | 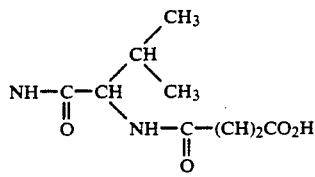 |
| 142 | " | 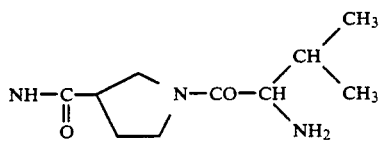 |
| 143 | " | 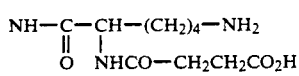 |
| 144 | " | 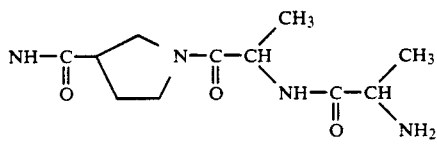 |
| 145 | " | 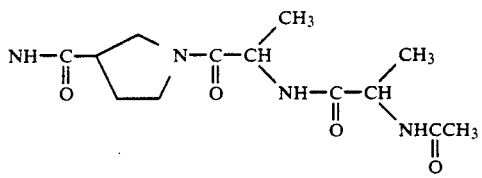 |
| 146 | $C_2H_5$ | Br |
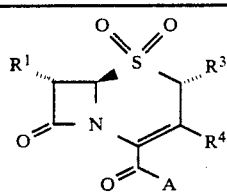
| No. | A | $R^1$ | $R^3$ | $R^4$ |
|---|---|---|---|---|
| 147 | $C_2H_5$ | $OCH_3$ | H | $CH_3$ |
| 148 | Ph | Cl | H | $CH_3$ |
| 149 | $-CH=CH-CH_3$ | Cl | H | $CH_2OCOCH_3$ |
| 150 | $^tC_4H_9$ | Cl | H | 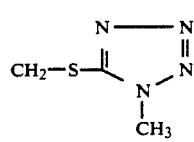 |
| 151 | " | $OCH_3$ | H | " |
| 152 | " | Cl | H | 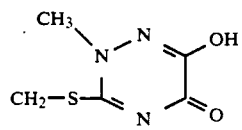 |
| 153 | " | $OCH_3$ | H | " |

-continued

| No. | | | | |
|---|---|---|---|---|
| 154 | " | OCH₃ | Br | tetrazole with CH₂—S— substituent and N—CH₃ |
| 155 | " | OCH₃ | H | thiadiazole with CH₂—S— and —SCH₂CO₂H substituents |
| 156 | ⁱC₄H₉ | OCH₃ | H | fused pyridazine-tetrazole with CH₂—S— and CO₂H |
| 157 | " | " | " | tetrazole with CH₂—S— and N—CH₂CH₂CH₂CO₂H |
| 158 | " | " | " | CO₂H |
| 159 | cyclopentyl | " | " | triazinone with CH₃—N, CH₂—S—, CO₂H/OH and =O |
| 160 | " | " | " | tetrazole with CH₂—S— and N—CH₃ |
| 161 | " | " | " | CO₂H |
| 162 | cyclopentyl-CO₂H | " | " | fused pyridazine-tetrazole with CH₂—S— |
| 163 | CMe₂Ph | " | " | CH₂OCOCH₃ |
| 164 | CMe₂Ph | OCH₃ | H | tetrazole with CH₂—S— and N—CH₃ |
| 165 | " | " | " | triazinone with CH₃—N, CH₂—S—, CO₂H/OH and =O |
| 166 | C≡C—Ph | " | " | tetrazole with CH₂—S— and N—CH₃ |
| 167 | " | " | " | CO₂H |

| 168 | " | " | " | 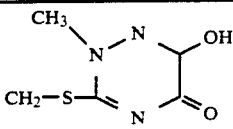 |

Preparation of the compounds of the invention

The compounds of the present invention can be prepared by a process which comprises:

(1) in any order, converting the carboxyl group —$CO_2H$ at the 4-position of the cephem nucleus or at the 3-position of the penam nucleus of a compound of formula (IIa) or (IIb), respectively:

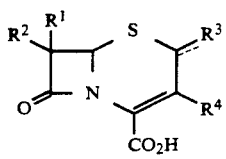 (IIa)

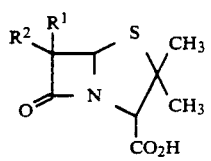 (IIb)

wherein $R^1$, $R^2$, $R^3$ and $R^4$ are as defined above, into a carbonyl group —C(O)A, wherein A is as defined above, and oxidizing the sulphur atom at the 1-position of the said cephem or penam nucleus to the desired sulphone oxidation level; and (2) if desired, converting the resulting compound of formula (Ia) or (Ib) into a pharmaceutically or veterinarily acceptable salt thereof.

In the conversion step, the carboxylic moiety is typically activated as the acyl halide, anhydride, mixed anhydride, thioester or ester thereof, and then reacted with a synthetic equivalent of $A^-$, wherein A is as defined above. Suitable synthetic equivalents of $A^-$ include the following organometallic derivatives of A:

A-MgX (Grignard reagents);
A-Li (organolithium reagents e.g. phenyllithium);
$A_2CuLi$ (lithium dialkylcopper reagents);
A(PhS)CuLi (lithium phenylsulphenyl (alkyl)copper reagents);
A-Cu (cuprous reagents; e.g. cuprous acetylides);
$A_2Cd$ (organocadmium reagents);
AZnBr (organozinc reagents);
$ARh^I(CO)(Ph_3P)_2$ (bis-(triphenylphosphine)carbonylalkylrhodium (I) reagents); and
$A_nSnX_{(4-n)}$ (organotin reagents, wherein X is $C_1$-$C_{12}$ alkyl, chloro, phenyl, and n may be 0, 1, 2, 3, 4).

When A is hydrogen, suitable synthetic equivalents of $A^-$ are mixed hydrides, in particular organoboron, organoaluminum or organotin hydrides, e.g. bis(triphenylphosphine)copper (I) borohydride, tri-tert-butoxyaluminum hydride and tributyltin hydride.

When A is $CHN_2$, the synthetic equivalent of $A^-$ is diazomethane. The compounds wherein A is $CHN_2$ may be in turn converted into the corresponding compounds wherein A is $CH_2Cl$ (by reaction with HCl in an inert organic solvent, e.g. $CH_2Cl_2$, ether or acetone), $CH_2I$ (by reaction with $I_2$), $CH_2OH$ (by reaction with $H_2SO_4$ in dioxane-water), $CH_2OCH_2$ (by reaction with $BF_3.Et_2O$ in methanol), $CH_2OCOR'$ wherein R' is as defined above (by reaction with $R'CO_2H$), $CH_2OSO_2R'$ (by reaction with $R'SO_2H$) or $CH_3$ (by reaction with excess 47% HI).

The conditions of the above-stated reactions are described or referred to in major textbooks (see among others, J. March, "Advanced Organic Chemistry", McGraw-Hill) and can vary widely according to the individual substrate and group A.

In the oxidation step, the compounds are oxidized to the corresponding sulphones. Preferred oxidizing agents are peracids in an inert organic solvent or in a mixture of water and an organic solvent. Suitable peracids are, for example peracetic acid, m-chloroperoxybenzoic acid (MCPBA), monoperphthalic acid; suitable solvents are chloroform, dichloromethane, tetrahydrofuran (THF) and ethanol. Another oxidizing agent, preferably used for penam substrates, is potassium permanganate in a mixture of water and acetic acid.

It is understood that in the process above any functional group, if needed or desired, can be masked by conventional methods and unmasked when convenient. Also, it is understood that a group $R^4$ can be converted by conventional methods into a different group $R^4$ included within those previously defined, if desired, at the end or at any stage of the process above. These conversions or masking/unmasking of the protecting groups are well known on cephems IIa and their sulphones.

Compounds IIa and IIb, are known compounds or can be be prepared from known compounds by known methods.

Uses of the compounds of the invention

The potentialities of protease inhibitor therapy in the treatment of conditions resulting from the destruction of connective tissues have recently received particular attention. Much effort has been devoted to the search for inhibitors of human leukocyte elastase (HLE), which is the primary destructive agent in pulmonary emphysema and is probably involved in rheumatoid arthritis (J. C. Power, Am. Rev. Resp. Diseases 127, S54-S58, 1983; C. H. Hassal et al, FEBS Letters, 183, n 2, 201, 1985, G. Weinbaum and V. V. Damiano, TIPS, 8, 6, 1987; M. Velvart, Rheymatol. Int., 1, 121, 1981).

Low molecular weight protease inhibitors appear to have a number of advantages over natural high molecular weight protease inhibitors from either plant or animal sources. (1) They can be obtained in sufficient quantities. (2) They can be rationally designed or optimized. (3) They are not antigenic. And (4) They may be used orally or in aerosols.

Many low molecular weight elastase inhibitors discovered so far contain reactive functional groups (chloromethyl ketones, isocyanates, etc). They may react with the functional groups of proteins, and therefore they may be quite toxic. In this respect, β-lactam compounds are of potential interest because, though reactive towards serine protease, they are, as it is known, non-toxic at very high concentrations.

The compounds of the present invention are characterized by high inhibitory activity on HLE. When tested in vitro, they display advantages over previously known β-lactam inhibitors. Moreover, their chemical stability at physiological pH is unexpectedly good, which foreshadows further advantages under in vivo conditions.

Thus, for example, Compound 51 (Example 4) favorably compares with the corresponding cephalosporanic ester (Reference) in terms of increased chemical stability ($t_{\frac{1}{2}}$), higher rate of formation of the HLE complex ($K_{on}$), lower dissociation rate ($K_{off}$), and better "efficiency" (lower apparent dissociation constant of HLE-inhibitor complex at steady state, $K_i^{ss}$)

| Compound | Chemical stability[a] $t_{\frac{1}{2}}$ (h) | HLE-inhibition Kineticparameters[b] | | |
|---|---|---|---|---|
| | | $K_{on}$ ($10^4 M^{-1} s^{-1}$) | $K_{off}$ ($10^{-3} s^{-1}$) | $K_i^{ss}$ (nM) |
| Comp. 51 n = 0 | 19.3 | 2.0 | 2.6 | 11 |
| Reference n = 1 | 3.2 | 0.9 | 3.5 | 18.4 |

(a) Chemical stability at 37° C., 0.05M pH 7.4 phosphate buffer (5% DMSO as solubilizing vehicle) was determined by following the time course of starting material depletion (pseudo-fast order kinetics; 10 mM initial conc.) by HPLC analysis (stationary phase Whatman Partisphere 5 C18, 110×4.7 mm i.d., mobile phase A, pH 2.5 0.1M phosphate buffer; mobile phase B, 60:40 phase A/MeCN; UV detection at λ=254 nm;

(b) Kinetic parameters of HLE (Calbiochem. Lot 702738) were determined at 37° C., 0.027M pH 7.4 phosphate buffer, 1% DMSO, 1% MeCN, NaCl (I=0.15), by monitoring the release of 7-amino-4-methylcoumarin (fluorence detection) from N-methoxysuccinyl-alanyl-propyl-valyl-7-amido-4-methylcoumarin as the substrate, according to the equations:

$$[P] = V_s t + \frac{(V_z - V_s)}{K} \cdot (1 - e^{kt})$$

$$K = K_{off} + \frac{K_{on} \cdot [I]}{1 + [S]/K_m}$$

$$V_s = V_o \cdot \frac{1 + [S]/K_m}{1 + [S]/K_m + [I]/K_i^{ss}}$$

wherein:
[P], [I], [S] = product, inhibitor, and substrate concentration
$V_s$ = steady state rate
$V_z$ = zero time rate
$V_o$ = rate at [I] = O
Km = Michaelis constant for the enzyme-substrate pair (independently determined under the same experimental conditions).

Owing to their high elastase-inhibiting activity and their quite negligible toxicity, the compounds of the present invention can be used in the treatment of inflammatory and degenerative diseases caused by proteolytic enzymes in mammals including humans. The compounds can be used to make medicaments useful to prevent or arrest the progression of diseases cause by proteolytic degradation of lungs and connective tissues, reduce inflammation and fever, and relieve pain. Such diseases are emphysema, acute respiratory distress syndrome, bronchial inflammation, rheumatoid arthritis, osteoarthritis, infectious arthritis, rheumatic fever, spondylitis, gout, lupus, psoriasis, and the like.

Accordingly, the present invention also provides pharmaceutical and veterinary compositions containing a suitable carrier and/or diluent and, as an active principle, a 4-acylcephem sulphone of formula (Ia) or 3-acylpenam sulphones of formula (Ib) or a pharmaceutically or veterinarily acceptable salt thereof. The pharmaceutical or veterinary compositions containing a compound of formula (Ia) or (Ib) or salt thereof may be prepared in a conventional way by employing conventional non-toxic pharmaceutical carriers or diluents in a variety of dosage forms and ways of administration.

The compounds of formula (Ia), (Ib) can be administered: orally, parenterally, by inhalation, rectally or topically.

Oral administration may be, for example, as tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets.

These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc.

The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Formulation for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions.

Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives.

Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents.

Syrups and elixirs may be formulated with sweetening agents, for example glycerol, sorbitol or sucrose. Such formulations may also contain a demulcent, a preservative and flavoring and coloring agents.

Parenteral administration may be achieved either subcutaneously, or intravenously, or intramuscularly, or intrasternally, or by infusion techniques, in the form of sterile injectable aqueous or oleagenous suspensions. The pharmaceutical compositions may be in the form of a sterile injectable aqueous or oleagenous suspension. This suspension may be formulated using known techniques using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oil may be employed including synthetic mono- or diglycerides. In addition fatty acids such as oleic acid find use in the preparation of injectables.

Administration by inhalation involves the use of aerosols or solutions for nebulizers.

Rectal administration involves the use of suppositories prepared by mixing the drug with a suitable non-irritating excipient which is solid at ordinary temperature but liquid at the rectal temperature and will therefore melt in the rectum to release the drug. Such materials are cocoa butter and polyethylene glycols.

Topical administration involves the use of creams ointments, jellies, solutions or suspensions.

Still a further object of the present invention is to provide a method of controlling inflammatory and degenerative diseases by administering a therapeutically effective amount of one or more of the active compounds encompassed by the formula (I) in humans or mammalians in need of such treatment.

Daily dose are in the range of about 0.5 to about 100 mg per kg of body weight, according to the activity of the specific compound, the age, weight and conditions of the subject to be treated, the type and severity of the disease, and the frequency and route of administration. Preferably, daily dosage levels for humans are in the range of 50 mg to 2 g.

The amount of active ingredient that may be combined with the carrier materials to produce a single dosage form will vary depending upon the host treated and the particular mode of administration.

For example, a formulation intended for the oral administration to humans, may contain from 5 mg to 2 g of active agent compounded with an appropriate and convenient amount of carrier material which may vary from about 5 to about 95 percent of the total composition. Dosage unit forms will generally contain between from about 25 mg to about 500 mg of active ingredient.

Having generally described this invention, a further understanding can be obtained by reference to certain specific examples which are provided herein for purposes of illustration only and are not intended to be limiting unless otherwise specified.

EXAMPLES

Example 1

($7\alpha$)-Chloro-4-ethylcarbonyl-3-methyl-3-cephem 1,1-dioxide (Compound 33)

A solution of ($7\alpha$)-chloro-3-methyl-3-cephem-4-carboxylic acid (515 mg) in 30 ml of dry benzene was stirred a 7° C. for 45 min with oxalyl chloride (0.38 ml).

Removal of the volatile materials in vacuo afforded crude ($7\alpha$)-chloro-4-chlorocarbonyl-3-methyl-3-cephem; IR (KBr) max 1780 br, 1750 cm$^{-1}$.

This material was taken up in dry ether and treated under nitrogen at $-70°$ C. with aluminum trichloride (195 mg) and 2M ethereal ethylmagnesium bromide (1.5 ml). After 5 min, the reaction mixture was poured into ice-water and washed in sequence with aq. NaHCO₃ and brine. The organic phase was dried over Na₂SO₄ and concentrated in vacuo to afford (7α)-chloro-4-ethylcarbonyl-3-methylcephem as a mixture of 3 and 2=isomers (210 mg).

The mixture above was dissolved in a mixture of 0.05M pH7 phosphate buffer and ethyl acetate (1:2, total volume 9 ml) and treated at 0°–5° C. with m-chloroperoxybenzoic acid (385 mg). After stirring at room temperature for 1 h, the reaction mixture was poured into ice-water and washed in sequence with aqueous sodium metabilsulphite, aq. sodium hydrogen carbonate and brine. Drying over Na₂SO₄, removal of the solvent and silica gel chromatography of the residue afforded the pure title compound (90 mg) as a syrup.

IR (CHCl₃) νmax 1780,1690 cm⁻¹.

Example 2

4-tert-Butylcarbonyl-(7α)-methoxy-3-methyl-3-cephem 1,1-dioxide (Compound 49)

A solution of (7α)-methoxy-3-methyl-3-cephem-4-carboxylic acid (1.68 g) in dry benzene (100 ml) was treated at 7° C. with dry DMF (few drops) and oxalyl chloride (1.26 ml). After stirring for 45 min, removal of the volatile materials in vacuo afforded crude 4-chlorocarbonyl-(7α)-methoxy-3-methyl-3-cephem.

This material was taken up in dry THF (50 ml) and treated at −70° C. under nitrogen with aluminium trichloride (195 mg) and 1.43M ethereal tert-butylmagnesium chloride (5.13 ml).

After stirring for 15 min at −50° C. the reaction mixture was poured into ice-water, washed in sequence with aq. NaHCO₃ and brine, and evaporated to dryness, to yield crude 4-tert-butylcarbonyl-(7α)- methoxy-3-methylcephem.

A portion (300 mg) of the material above was dissolved in ethyl acetate (70 ml) and treated at r.t. with m-chloroperoxybenzoic acid (570 mg). After 1.5 h, the reaction mixture was washed in sequence with aq. NaHSO₃, aq. NaHCO₃ and brine. Drying over Na₂SO₄, removal of the solvent and silica gel chromatography of the residue afforded the pure title compound (114 mg) as a white powder, mp 128° C.

IR (CHCl₃) νmax 1785, 1685 cm⁻¹

NMR (200 MHz, CDCl₃) δ 1.26(9H,S9), 1.70(3H,s), 3.51 and 3.93 (2H, each d,J=18 Hz), 3.56(3H,S), 4.66 and 5.16 (each 1H,d,J=1.6 Hz) ppm MS (FD) 301 m/z(M⁺)

Example 3

3-Bromomethyl-4-tert-butylcarbonyl-(7α)-methoxy-3-cephem 1,1-dioxide (Compound 50)

A solution of 4-tert-butylcarbonyl-(7α)-methoxy-3-methyl-3-cephem 1,1-dioxide (see Example 2; 130 mg), N-bromosuccinimide (NBS; 100 mg), and α,α′-azoisbutyronitrile (AIBN, 5 mg) in carbon tetrachloride (20 ml) and dichloromethane (15 ml) was refluxed for 2 h. Removal of the solvent and silica gel chromatography afforded the title compound (130 mg) as a white powder.

IR (CHCl₃) νmax 1790, 1690 cm⁻¹

NMR (200 MHz, CDCl₃) δ 1.31 (9H,s), 3.56 (3H,s), 3.58 (1H, d, J=14.6 Hz), 3.79 and and 3.91(2H, each d,J=11.4 Hz), 4.28(1H,dd,J=14.6 and 1.4 Hz), 4.76(1H,dd,J=1.9 and 1.4 Hz), 5.20(1H,d,J=1.9 Hz)

MS (FD) 379 m/z (M⁺)

Example 4

3-Acetoxymethyl-4-tert-butylcarbonyl-(7α)-methoxy-3-cephem 1,1-dioxide (Compound 51)

A solution of 3-bromomethyl-4-tert-butylcarbonyl-(7α)-methoxy-3-cephem 1,1-dioxide (see Example 3; 93 mg) in dry acetonitrile (5 ml) wa stirred at room temperature for 1 h in the presence of acetic acid (0.15 ml) and silver acetate (118 mg).

The reaction mixture was taken up in EtOAc and sequentially washed with aq. NaHCO₃ and brine. Drying over Na₂SO₄ and removal of the solvent, followed by silica gel chromatography, afforded the title compound (45 mg) as a white powder, mp 134° C.

IR (KBr) νmax 1780,1732,1687 cm⁻¹.

NMR (200 MHz,CDCl₃) δ 1.28(9H,s), 2.08(3H,s), 3.57(3H,s), 3.83(1H,d,J=18.5 Hz), 4.00(1H,dd,J=18.5 and 1.5 Hz), 4.43 (2H,ABq,separation of inner lines=1.9 Hz), 4.73 (1H,dd,J=1.9 and 1.5 Hz), 5.20(1H,dd,J=1.9 Hz) ppm MS (FD) 359 m/z (M⁺)

Example 5

4-tert-Butylcarbonyl-(7α)-chloro-3-methyl-3-cephem 1,1-dioxide (Compound 1)

A solution of (7α)-chloro-4-chlorocarbonyl-3-methyl-3-cephem (see Example 1; 2.32 g) in dry THF (80 ml) was sequentially treated with copper (I) iodide (2.076 g) and 2 M ethereal tert-butylmagnesium chloride (4.95 ml) at −70° C. under nitrogen.

The reaction mixture was left rise to −50° C. and then poured into ice-water. After 10 min stirring, extraction with ethyl acetate, washing of the organic layer with aq. NaHCO₃, drying over Na₂SO₄ and removal of the solvent left crude 4-tert-butylcarbonyl-(7α)-chloro-3-methylcephem.

This material was passed through a short silica gel column and then treated with m-chloroperoxybenzoic acid (2.5 g) in ethyl acetate at 10° C. overnight. The reaction mixture was diluted with ethyl acetate, sequentially washed with aq. NaHSO₃, aq. NaHCO₃, aq. NaCl, dried (Na₂SO₄), concentrated in vacuo, and purified by silica gel chromatography to afford the title compound (550 mg) as a white powder, mp 218° C.

IR (KBr) νmax 1773,1687 cm⁻¹

NMR (200 MHz, CDCl₃,) δ 1.26(9H,s), 1.72(3H,s), 3.60(1H,d,J=18.1 Hz), 3.96(1H,dd,J=18.1 and 1.3 Hz), 4.76(1H,dd,J=1.3 and 1.7 Hz), 5.32(1H,d,J=1.7 Hz) ppm

Example 6

3-Bromomethyl-4-tert-butylcarbonyl-(7α)-chloro-3-cephem 1,1-dioxide (Compound 2)

A solution of 4-tert-butylcarbonyl-(7α)-chloro-3-methyl-3-cephem 1,1-dioxide (see Example 5; 150 mg) in carbon tetrachloride (40 ml) was refluxed for 4 h in the presence of NBS (114 mg) and AIBN (2 mg).

Removal of the solvent and chromatography afforded the title compound (112 mg; plus 40 mg of starting material) as a white powder, mp 155° C.

IR (KBr) νmax 1795,1690 cm⁻¹

MS (FD) 383 m/z (M⁺)

NMR (200 MHz,CDCl₃) δ 1.31(9H,s), 3.65(1H,d,J=18.1 Hz), 3.85(2H,ABq J=11.4 Hz), 4.32(1H,dd,J=11.4 and 1.3 Hz), 4.88(1H,dd,J=1.8 and 1.3 Hz), 5.37(1H,d,J=1.8 Hz) ppm

Example 7

3-Acetoxymethyl-4-tert-butylcarbonyl-(7α)-chloro-3-cephem 1,1-dioxide (Compound 3)

A solution of (7α)-chlorocephalosporanic acid (50 g) in dichloromethane (450 ml) and ethanol (150 ml) was treated under stirring with m-chloroperoxybenzoic acid (80 g) overnight at 0° C. and for 4 h at room temperature.

The reaction mixture was washed with aq. $NaHSO_3$, and the solvent from the organic layer removed in vacuo. The residue was dissolved in ether (400 ml) and left crystallize overnight in the refrigerator to obtain (7α)-chlorocephalosporanic acid 1,1-dioxide (28 g) as a white powder;

IR (KBr) νmax 3400 br,1800,1740–1715 $cm^{-1}$

NMR (90 MHz,$CDCl_3$): δ 2.08(3H,s), 3.90(2H,ABq,J=18 Hz), 4.85(1H,d, J=1.5 Hz), 4.93(2H,ABq,J=13.5 Hz), 5.28 (1H,d,J=1.5 Hz), 9.73(1H,br s, exch. D=0) ppm The above product (732 mg) in dry THF (20 ml) was allowed to react with oxalyl chloride (0.15 ml) in the presence of dimethylformamide (DMF; few drops) at 7° C. under nitrogen. The reaction mixture was left rise to room temperature and after 1.5 h cooled to −70° C. Copper (I) iodide (453 mg) and, after 15 min stirring, 2M ethereal tert-butylmagnesium chloride (2.5 ml) were added under nitrogen. The temperature was let rise to −10° C. and the reaction mixture was poured into ice water. After filtration, the resulting solution was partitioned between ethyl acetate and aq. $NaHCO_3$. The organic layer was dried and evaporated. Silica gel chromatography of the residue afforded the title compound (250 mg) as a white powder, mp 168° C.

IR (KBr) νmax 1788,1732,1690 $cm^{-1}$

NMR (200 MHz,$CDCl_3$) δ 1.28(9H,s), 2.09(3H,s), 3.74(1H,d,J=18.1 Hz), 4.02(1H,dd,J=18.1 and 1.0 Hz), 4.45(2H,ABq,J=13.4 Hz), 4.84 (1H,dd,J=1.8 and 1.5 Hz), 5.36(1H,d,J=1.8 Hz) ppm MSD (FD) 363 m/z ($M^+$)

Example 8

3-Acetoxymethyl-4-benzylcarbonyl-(7α)-chloro-3-cephem 1,1-dioxide (Compound 35)

A solution of (7α)-chlorocephalosporanic acid 1,1-dioxide (see Example 10; 1 g) in dry THF (20 ml) was treated, in sequence, with oxalyl chloride (0.364 ml), copper (I) iodide (620 mg), and 2M benzylmagnesium chloride in THF (1.6 ml), according to the experimental procedure detailed in Example 10.

Workup and chromatography afforded the title compound as a white powder (150 mg); mp 147° C.

IR (KBr) νmax 1795,1735,1705 $cm^{-1}$ $^1$H NMR (200 MHz, $CDCl_3$) δ 2.07(3H,s), 3.79(2H,ABq,J=18.1 Hz), 4.07 (2H,s), 4.17(1H,d,J=1.7 Hz), 4.53 and 5.00(2H, each d,J=14.4 Hz), 5.30(1H,d,J=1.7 Hz), 7.17–7.38(5H,m) ppm $^{13}$C NMR (50 MHz,$CDCl_3$) δ 20.49($OCOCH_3$), 48.70 and 51.25($COCH_2Ph$ and $C_2$), 56.17($C_7$), 61.29($CH_2OCOCH_3$), 70.65($C_6$), 125.52($C_3$), 127.72(phenyl $C_4$), 129.10 and 129.40(phenyl $C_2$, $C_3$, $C_5$, $C_6$), 131.20 and 132.44($C_4$ and phenyl C,), 158.85(β-lactam), 170.02($CH_2OCOCH_3$), 193.01($CH_2Ph$) ppm MS (FD) 397 m/z ($M^+$)

Example 9

3-Acetoxymethyl-(7α)-chloro-4-ethylcarbonyl-3-cephem 1.1-dioxide (Compound 34)

By operating as indicated in Example 7, from (7α)-chlorocephalosporanic acid (538 mg), oxalyl chloride (0.20 ml), DMF (few drops), CuI (333 mg), and 2M ethereal ethylmagnesium bromide (0.88 ml), the title compound (85 mg) was obtained as a white powder; mp 168° C.

IR (KBr) νmax 1810,1730,1705 $cm^{-1}$

NMR (200 MHZ,$CDCl_3$) δ 1.17(3H,t,J=7.1 Hz), 2.08(3H,S) 2.75 and 2.88 (2H, each q, J=7.1 Hz), 3.74 and 4.02 (2H, each d, J=18.4 Hz), 4.52 and 4.98(2H, each d,J=14.3 Hz), 4.86 and 5.36 (each 1H.d.J=1 7 Hz) ppm

Example 10

3-Acetoxymethyl-(7α)-chloro-4-formyl-3-cephem 1,1-dioxide (Compound 39)

A solution of (7α)-chlorocephalosporanic acid 1,1-dioxide (see Example 7; 323 mg) in dry THF (8 ml) was treated at −20° C. with oxalyl chloride (0.172 ml) in the presence of DMF (1 drop). The reaction mixture was left rise to room temperature. After 1 h the volatile materials were removed, the residue was taken up in dichloromethane (2 ml)/benzene (6 ml), and tributyltin hydride (0.269 ml) was than added. After stirring for 30 min at room temperature, the reaction mixture was concentrated and residue partitioned between acetonitrile and n-hexane. The lower layer was collected and evaporated to leave a residue which was purified by silica gel chromatography to yield the title compound (200 mg) as a syrup;

IR ($CHCl_3$) νmax 2800,1810,1740 br $cm^{-1}$

NMR (90 MHz, $CDCl_3$) δ 2.10(3H,s), 4.10(2H,ABq,J=18 Hz), 4.90(1H,d, J=2 Hz), 5.05(2H,s), 5.40(1H,d,J=2 Hz), 10.00(1H,s) ppm MS(FD) 307 m/z ($M^+$).

Example 11

(6α)-Bromo-3-ethylcarbonylpenam 1,1-dioxide (Compound 146)

A solution of 6,6-dibromopenicillanic acid (7.18 g) in dichloromethane was treated at −20° C. with 2-pyridyldisulphide (4.41 g) and triphenylphospine (5.24 g). The reaction mixture was allowed to warm up to ambient temperature, the solvent was removed in vacuo and the residue (consisting of the crude 2-pyridyl thioester of the starting material) was allowed to react at −75° C. in THF (110 ml) with 2M ethereal ethylmagnesium bromide (15.5 ml). After 35 min the reaction was quenched with saturated aq. $NH_4Cl$ and extracted with 1:2 ethyl acetate/isopropyl ether. The organic extracts were washed twice with water, dried over $Na_2SO_4$ and concentrated. Silica gel chromatography afforded (6α)-bromo-3-ethylcarbonylpenam (1.3 g) as a white solid, mp 68–69° C.

IR ($CHCl_3$) νmax 1780,1710 $cm^{-1}$

NMR (90 MHz,$CDCl_3$) δ 1.10(3H,t,J=7.5 Hz), 1.37 and 1.70 (each 3H,s) 2.62 and 2.67 (2H, each q,J=7.5 Hz), 4.40(1H,s), 4.85 and 5.41 (each 1H,d,J=2 Hz) ppm This material (100 mg) in dichloromethane (5 ml) was stirred for 5 h at 25° C. in the presence of m-chloroperoxybenzoic acid (293 mg). The reaction mixture was sequentially washed with aq. $NaHSO_3$ and aq. $NaHCO_3$. After removal of the solvent in vacuo, flash chromatography afforded the title product as a yellowish powder (80 mg); mp 117°-118° C.

IR (KBr) $\nu$max 1793,1712 cm$^{-1}$

NMR (90 MHz,CDCl$_3$) $\delta$ 1.10(3H,t,J=7.5 Hz), 1.38 and 1.62 (each 3H,s), 2.70(2H,q,J=7.5 Hz), 4.20(1H,s), 4.70 and 5.21 (each 1H,d,J=1.7 Hz) ppm

Example 12

(6α)-Chloro-3-ethylcarbonylpenam 1,1-dioxide (Compound 116)

A solution of sodium (6α)-chloropenam-3-carboxylate (543 mg) in dry THF was allowed to react at −5° C. for 1 h with oxalyl chloride (0.18 ml) in the presence of DMF (1 drop). The reaction mixture was evaporated to dryness, taken up in dry THF (10 ml), cooled under nitrogen to −78° C. and treated with copper (I) iodide (402 mg) and 2M ethereal ethylmagnesium bromide (1.06 ml). After stirring for 15 min, the reaction mixture was poured into ice water and extracted with ether. The extracts were washed with aq. NaHCO$_3$, dried and evaporated. Silica gel chromatography afforded (6α)-chloro-3-ethyl-carbonylpenam (50 mg) as a syrup.

IR (CHCl$_3$) $\nu$max 1778,1705 cm$^{-1}$

NMR (200 MHz, CDCl$_3$) $\delta$ 1,05(3H,t,J=7.1 Hz), 1.41 and 1.62 (each 3H,s), 2.58 and 2.62 (2H, each q,J=7.1 Hz), 4.36(1H,s), 4.77 and 5.29 (each 1,d,J=1.3 Hz) ppm.

The above material (20 mg) was dissolved in ethyl acetate (1 ml) and allowed to react with m-chloroperoxybenzoic acid (81 mg) for 6 h at room temperature. Washing with 1M aq. NaHSO$_3$, sat. aq. NaHCO$_3$ and brine, followed by removal of the solvent and silica gel chromatography, afforded the title material as a foam (17 mg);

IR (CHCl$_3$) $\nu$max 1805,1715 cm$^{-1}$

NMR (200 MHz, CDCl$_3$) $\delta$ 1.08(3H,t,J=7.1 Hz), 1.39 and 1.62 (each 3H,s), 2.66 and 2.71 (2H, each q,J=7.1 Hz), 4.19 (1H,s), 4,65 and 5.19 (each 1H,d,J=1.7 Hz) ppm

Example 13

4-Ethylcarbonyl-7α-methoxy-3-methyl-3-cephem 1,1-dioxide (Compound 147)

A solution of 7α-methoxy-3-methyl-3-cephem-4-carbonyl chloride (0.7 g), prepared as described in Example 2, in dry distilled ethyl ether (20 ml), was treated at −70° C. under nitrogen with copper iodide (I) (0.54 g).

After 10 minutes stirring, a 2M ethereal solution of ethylmagnesium bromide (2 ml) was dropped into the reaction mixture. The reaction mixture was left rise to −50° C. and then poured into ice-water. Extraction with ethyl acetate, washing with aqueous NaHCO$_3$ and removal of the solvents left a residue, which was purified by flash-chromatography (SiO$_2$, EtOAc/hexane) and then treated with m-chloroperoxybenzoic acid (1.5 g) in cold (0° C.) ethyl acetate. The reaction mixture was stirred at 10-15° C. for 1 h, then sequentially washed with aqueous NaHCO$_3$, aqueous NaHCO$_3$ and aqueous NaCl. Drying over Na$_2$SO$_4$ and removal of the solvent, followed by flash-chromatography, afforded the title compound (150 mg) as a light yellow oil.

IR (CHCl$_3$) $\lambda$max 1780, 1685 cm$^{-1}$

NMR (200 MHz, CDCl$_3$) $\delta$ 1.13 (3H, t, J=7.1 Hz), 1.96 (3H,s), 2.66 and 2.90 (2H, each dq, J=18 and 7.1 Hz), 3.59 (3H, s), 3.60

(1H, d, J=17.6 Hz), 3.85 (1H, dt, J=17.6 and 1.2 Hz), 4.65

(1H, dd, J=1.4 and 1.2 Hz), 5.14 (1H, d, J=1.4 Hz) ppm.

Example 14

7α-Chloro-3-methyl-4-phenylcarbonyl-3-cephem 1,1-dioxide (Compound 148)

A solution of 7α-chloro-3-methyl-3-cephem-4-carboxylic acid 1,1-dioxide (1.6 g) in THF was treated at 5~10° C. with oxalyl chloride (0.52 ml) and DMF (2 drops). After 1 hour, the reaction mixture was cooled at −70° C. copper iodide (1.14 g) was added and then phenyl magnesium bromide (2M THF solution, 3 ml) was slowly added under stirring. After 0.7 h at −70° C., the reaction mixture was poured into ice-water. Extraction with ethyl acetate, washing of the organic layer with aqueous NaHCO$_3$, drying over Na$_2$SO$_4$ and removal of the solvent left the crude title product, which was then obtained pure (150 mg) as a white powder after flash-chromatography.

Mp 184-186° C.

IR (KBr) $\lambda$max 1780, 1677 cm$^{-1}$

NMR (200 MHz) $\delta$ 1.67 (3H, s), 3.66 (1H, d, J=18.3 Hz)

4.03 (1H, dt, J=18.3 and 1.43 Hz), 4.91 (1H, dd, J=1.87 and 1.43 Hz), 5.33 (1H, d, J=1.87 Hz), 7.48-7.94 (5H, m) ppm.

Example 15

3-Acetoxymethyl-7α-chloro-4-phenylcarbonyl-3-cephem-1,1-dioxide (Compound 38)

Starting from 3-acetoxymethyl-7α-chloro-3-cephem-4-carboxylic acid 1,1-dioxide (500 mg) and following the experimental procedure described in Example 14, the title product was obtained as a yellowish powder (60 mg).

IR (CHCl$_3$) $\lambda$max 1790, 1735, 1670 cm$^{-1}$

NMR (200-MHz, CDCl$_3$) $\delta$ 1.97 (3H, s), 3.80 (1H, d, J=18.4 Hz), 4.11 (1H, dd, J=18.4 and=1 Hz), 4.42 (2H, ABq, J=13.5 Hz), 4.96 (1H, dd, J=2.0 and=1 Hz), 5.37 (1H, d, J=2 Hz), 7.47-7.93 (5H, m) ppm.

Example 16

3-Acetoxymethyl-7α-chloro 4-[(E)-1-oxo-2-butenyl]-3-cephem 1,1-dioxide (Compound 149)

A solution of 7α-chloro cephalosporanic acid 1,1-dioxide (323 mg) in THF was treated 1 h at −20° C. with oxalyl chloride (2 mol equiv.) in the presence of a catalytic amount of DMF. The volatile materials were removed under vacuum and the residue taken up in C$_6$H$_6$-CH$_2$Cl$_2$ 1:1 (20 ml) was stirred 10 minutes at 20° C. with allyltributyltin (0.4 ml). Workup and chromatography afforded the title product as a white solid (110 mg).

Mp 121-124° C.;

IR (KBr) $\lambda$max 1810, 1735 1680 1625 cm$^{-1}$

NMR (200 MHz, CDCl$_3$) $\delta$ 1.99 (3H, dd, J=6.8 and 1.7 Hz)

2.06 (3H, s), 3.76 and 4.02 (2H, each d, J=18.4 Hz)

4.52 and 4.70 (2H, each d, J=13.6 Hz), 4.90 (1H, d, J=1.9 Hz), 5.35 (1H, d, J=1.9 Hz), 6.39 (1H, dq, J=15.5 and 1.7 Hz), 7.07 (1H, dq, J=15.5 and 6.8 Hz) ppm.

Example 17

4-Tert-butylcarbonyl-7α-chloro-3-(1-methyl-1,2,3,4-tetrazol-5-yl) thiomethyl-3-cephem 1,1-dioxide (Compound 150)

A solution of 3-bromomethyl-4-tert-butylcarbonyl-7α-chloro-3-cephem 1,1-dioxide (65 mg), prepared as in Example 6, in dry acetonitrile (5 ml) was treated with triethylamine (0.025 ml) and 5-mercapto-1-methyl-1,2,3,4-tetrazole (26 mg). An immediate reaction took place (TLC monitoring). The solvent was removed in vacuo and the residue purified by flash-chromatography, thereby obtaining the title product as a white powder (35 mg)

Mp 162–164° C.

IR (KBr) λmax 1790, 1690 cm$^{-1}$

NMR (200 MHz, CDCl$_3$) δ 1.26 (9H, s), 3.76 and 4.08 (2H, each d, J=14.3 Hz), 3.93 (3H,S), 4.01 (1H, d, J=17.9 Hz), 4.26 (1H, dd, J=17.9 and 0.9 Hz), 4.85 (1H, dd, J=1.7 and 0.9 Hz), 5.33 (1H, d, J=1.7 Hz) ppm.

EXAMPLE 18

4-Tert-butylcarbonyl(7α)-methoxy-3-(1-methyl-1,2,3,4-tetrazol-5-yl)thiamethyl-3-cephem 1,1-dioxide (Compound 151)

A solution of 3-bromomethyl-4-tert-butylcarbonyl-(7α)-methoxy-3-cephem 1,1 dioxide (52 mg), prepared as in Example 3, in dimethylformamide (1 ml) was treated with sodium 1-methyl-1,2,3,4-tetrazolyl-5-mercaptide (36 mg). After 10 min. the reaction mixture was diluted with ethylacetate and washed with brine. Removal of the solvent and flash chromatography afforded the title compound (30 mg) as a white powder; m.p. 60:62° C.

IR (Kbr) λmax 1790, 1690 cm$^{-1}$

NMR (200 MHz, CDCl$_3$) δ 1.2(9H, s), 3.78 and 4.05 (2H, each d, J=14.2 Hz), 3.56 (3H, s), 3.93 (3H, s), 3.93 (1H, d, J=17.8 Hz), 4.20 (1H, d, J=17.8 Hz), 4.75 (1H, br, s), 5.17 (1H, d, J=1.7 Hz) ppm.

EXAMPLE 19

4-Tert-butylcarbonyl-(7α)-methoxy-3-(2-methyl-5-oxo-6-hydroxy-2,5-dihydro-1,2,4 triazin-3yl)thiomethyl-3-cephem 1,1-dioxide (Compound 153).

A solution of 3-bromomethyl-4-tert-butylcabonyl-(7α)-methoxy-3-cephem 1,1dioxide (230 mg), prepared as in Example 3, in dry acetonitrile (50 ml) was treated with triethylamine (0.1 ml) and 3-mercapto-2-methyl-5-oxo-6-benzhydryloxy-2,5 dihydro-1,2,4 triazine (2.75 mg). After 20 min. the solvent was removed and the protected compound purified by silica gel chromatography.

It was dissolved in dichloromethane (2 ml) then anisole (0.025 ml) and trifluoroacetic (1 ml) were added. After 15 min. TFA was completely removed in vacuo and the residue taken up in dichloromethane (1 ml). Addition of isopropylether afforded the title compound (175 mg) as a white powder, mp 148–150° C.

IR (KBr) λmax 1790, 1690, 1640 (large) cm$^{-1}$.

NMR (200 MHz, CDCl$_3$) δ 1.28 (9H, s), 3.63 and 4.19 (2H, each d, J=14.1 Hz), 3.56 (3H, s), 3.74 (3H, s), 3.83 (1H, d, J=17.8 Hz), 4.09 (1H, d, J=17.8 Hz), 4.76 (1H, br,s), 4.17 (1H, d, J=1,7 Hz) ppm.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A 4-acylcephem sulphone of formula (Ia) or a pharmaceutically or veterinarily acceptable salt thereof:

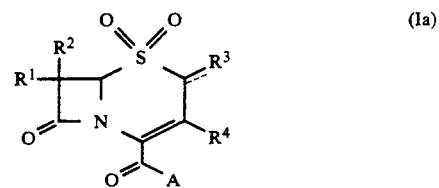

wherein:

A is a hydrogen atom or an organic radical selected from the group consisting of $C_1$–$C_{12}$ straight or branched alkyls; $C_2$–$C_{10}$ alkenyls; $C_2$–$C_{10}$ alkynyls; $C_6$–$C_{10}$ aryls; $C_3$–$C_8$ cycloalkyls; $C_5$–$C_8$ cycloalkenyls; $C_7$–$C_{22}$ aralkyls; $C_8$–$C_{12}$ aralkenyls; $C_8$–$C_{12}$ aralkynyls; $C_4$–$C_{20}$ (cycloalkyl)alkyls; 5- and 6-membered saturated and unsaturated heterocyclyl rings containing at least one heteroatom chosen from O, S and N; 5- and 6-membered saturated and unsaturated heterocyclyl rings fused to a 5- or a 6-membered heterocyclyl or to a $C_3$–$C_8$ cycloalkyl group; heterocycly-($C_{1-12}$)-alkyl, heterocycly-($C_2$–$C_{10}$)-alkenyl and heterocycly-($C_2$–$C_{10}$)-alkynyl wherein the heterocyclyl ring is selected from the group consisting of thiazolyl, triazolyl, thiadiazolyl, tetrazolyl, triazinyl, pyrrolyl, imidazolyl, furyl, thienyl, morpholinyl, pyranyl, pyridyl, pyrimidinyl, pyrazinyl, pyridazinyl and thiopyronyl;

wherein each of said organic radicals is unsubstituted or substituted by at least one substituent selected from the group consisting of halogen atoms; hydroxy; nitro; azido; diazo; —NH$_2$, —NHR' and —NR'R'', wherein R'and R'', which are the same or different, are $C_1$–$C_7$ straight or branched alkyl, phenyl or benzyl; —CHO; —SH; SR'; cyano; —CO$_2$H; —CO$_2$R'; —SO$_3$H; —C(O)R'; —C(O)CF$_3$; —CONH$_2$; —CONHCH$_3$; —CONH—CH$_2$CO$_2$H; —OCONH$_2$; —OC(O)R'; —OC(O)H; —C(O)R'; —OC(O)R'; —O—R'; —S—R'; —S(O)R'; —S(O)$_2$R'; —NHC(O)R'''; —NHC(O)OR''', wherein R''' is $C_1$–$C_7$ straight or branched alkyl, phenyl, benzyl, CH$_2$CH$_2$CO$_2$H or CH$_2$CH$_2$CH$_2$CO$_2$H; —NH—SO$_2$R'; —NHC(=NH)NH$_2$; $C_1$–$C_4$ alkyl; $C_2$–$C_4$ alkenyl; $C_2$–$C_4$ alkynyl; $C_3$–$C_6$ cycloalkyl; and substituted methyl which is one member selected from the group consisting of chloromethyl, fluoromethyl, difluoromethyl, trifluoromethyl, aminomethyl, azidomethyl, cyanomethyl, carboxymethyl, carbamoylmethyl, carbamoyloxymethyl, hydroxymethyl, $C_3$–$C_4$ alkoxycarbonylmethyl, and guanidinomethyl;

$R^1$ is:

(1) chloro, fluoro, bromo or iodo;
(2) a group A;
(3) a group —O—A;
(4) a group —S(O)$_n$A, wherein n is 0, 1 or 2;
(5) a group —OC(O)A;

(6) a group —O—SO₂A; or
(7) a group —NHC(O)A or an acylamino group, —NH—Z, wherein Z is a mono, di- or tripeptide composed of D or L α-aminoacid(s) chosen from the group consisting of Ala, Gly, Val, Leu, Ile, Phe and Pro, wherein the terminal amino group of said amino acid is either free, or acylated by a group —C(O)R''' or a group —C(O)OR''';

R² is hydrogen or:
(1) C₁-C₄ alkyl
(2) C₁-C₄ alkanoyloxy; or
(3) chloro, bromo or fluoro;

R³ is hydrogen or:
(1) C₁-C₄ alkyl;
(2) C₁-C₄ alkoxy;
(3) benzyl;
(4) halo; or
(5) a methylene group, =CH₂, or a group =CHR$^{IV}$, wherein R$^{IV}$ is C₁-C₄ alkyl, or phenyl, carboxy, or C₁-C₄ alkoxycarbonyl; and R⁴ is:
(1) a group A;
(2) chloro or fluoro;
(3) a group —O—A;
(4) a group —S(O)$_n$A;
(5) a group —C(O)A, —C(O)OA or —CO₂H;
(6) a group —CH₂—O—A;
(7) a group —CH₂S(O)$_n$A;
(8) a group —CH₂OC(O)A or —CH₂—O—Z;
(9) a group —CH₂SC(O)A;
(10) a group —CH₂—N(A)A' wherein A', being the same or different as A, is a group as defined for A; or A and A' taken together with the nitrogen atom to which they are attached represent a heterocyclic ring selected from the aforementioned group;
(11) a group

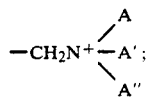

wherein A'', being the same or different or A or A', is as defined for A; or A is C₁-C₁₂ alkyl and A' and A'' together with the nitrogen atom to which they are attached represent a heterocyclic ring selected from the group consisting of piperidine, pyrrolidino, piperazine and morpholino; or A, A' and A'' together with the nitrogen atom to which they are attached represent pyridinio of the formula

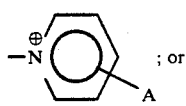 ; or

(12) a group —CH₂NH—C(O)A or —CH₂—NH—Z.

2. The compound of claim 1, having the formula (Ia')

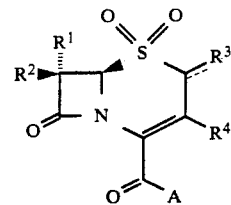

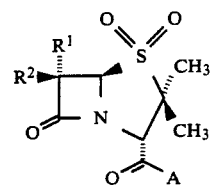

wherein
A is C₁-C₁₀ straight or branched alkyl, C₂-C₁₀ straight or branched alkenyl or alkynyl, C₃-C₈ cycloalkyl, dimethylphenyl, diphenylmethyl, phenyl or benzyl, wherein said alkyl, phenyl and benzyl groups are either unsubstituted or substituted by fluoro, chloro, carboxy, C₁-C₄ alkoxycarbonyl, carbamoyl, carbamoyloxy, methylsulphonyl, diazo, hydroxy, methoxy, ethoxy, tert-butoxy, benzyloxy, acetoxy, pivaloyloxy, benzoxy, or phenylacetoxy;

R¹ is:
(1') chloro, fluoro or bromo,
(2') C₁-C₄ alkyl, 1-(hydroxy)ethyl, 1-(benzyloxy)ethyl, 1-(benzyloxycarbonyloxy)ethyl, 1-(phenylacetoxy)ethyl, 2-fluoro-1-hydroxyethyl, isopropyl, phenyl or benzyl;
(3') methoxy, ethoxy, isopropoxy, phenoxy or benzyloxy;
(4') methylthio;
(5') formyloxy, acetoxy or phenylacetoxy;
(6') methyloxy or tosyloxy;
(7') formamido, acetamido, fluoroacetamido, trifluoroacetamido or chloroacetamido;
(8') R$^v$-Ala-NH, wherein R$^v$ is acetyl, tert-butoxycarbonyl, benzoxycarbonyl or HOOC—CH₂CH₂C(O)—;
(9') R$^v$-Val NH; or
(10') Val-Pro-NH, Lys-NH, or Al-Ala-Pro NH wherein the terminal amino group of Val, Lys or Ala respectively or the α-amino group of Lys is either free or acylated with a group R$^v$;

R² is hydrogen, chloro or fluoro;
R³ is hydrogen, methyl, benzyl, or bromo;
R⁴ is hydrogen or
(1') methyl, chloromethyl, bromomethyl or benzyl;
(2') chloro;
(3') methoxy or benzyloxy;
(4') methylthio;
(5') formyl, acetyl, benzoyl, carboxy, methoxycarbonyl, ethoxycarbonyl, tert-butoxycarbonyl or benzyloxycarbonyl;
(6') methoxymethyl, ethoxymethyl, isopropoxymethyl; or benzyloxymethyl, phenoxymethyl, 3-pyridyloxymethyl, wherein the phenyl and pyridyl rings are either unsubstituted or substituted by one group or two equal or different groups chosen from the group consisting of hydroxy, carboxy, amino and C₁-C₄ alkoxycarbonyls;

(7') methylthiomethyl, phenylthiomethyl, methylsulphonylmethyl, phenylsulphynylmethyl, phenylsulphonylmethyl or a group —CH$_2$—S—CH$_2$ —CH(NH$_2$)CO$_2$H wherein the amino group is either free or protected with tert-butoxycarbonyl or benzoxycarbonyl, acetyl and the carboxy group is either free or as the ethyl, tert-butyl, benzyl, methyl or diphenylmethyl ester;

(8') —CH$_2$-S-Het wherein Het is a heterocyclic ring chosen from:

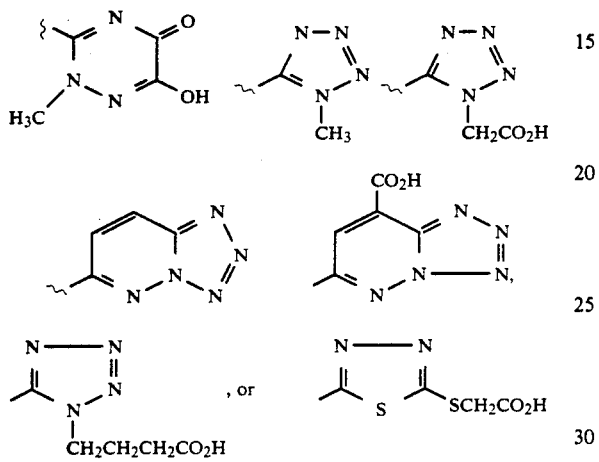

(9') acetoxymethyl, benzoxymethyl, phenyloacetoxymethyl or C$_3$–C$_{10}$ alkanoyloxymethyl which are either unsubstituted or substituted by one group or two equal or different groups selected from the group consisting of carboxy, hydroxy and amino, wherein the amino is free or acylated with a group selected from the group consisting of acetyl (Ac), benzoxycarbonyl (Cbz), tert-butoxycarbonyl (Boc), succinyl HOOCCH$_2$CH$_2$CO and glutaryl HOOC—CH$_2$—CH$_2$—CH$_2$—CO—;

(10') a group Z-OCH$_2$— wherein Z is Val-Pro, Ac-Val-Pro, Cbz-Val-Pro or Boc-Val-Pro;

(11') acetylthiomethyl;

(12') aminomethyl or C$_1$-C$_4$ alkylaminomethyl wherein the alkyl is either unsubstituted or substituted by a carboxy group;

(13') trialkylammoniomethyl wherein the alkyl group is chosen from the group consisting of methyl, ethyl, propyl, butyl and methyl, ethyl, propyl and butyl substituted by a carboxy group; alkyl(cycloalkyl)ammoniomethyl selected from the group consisting of:

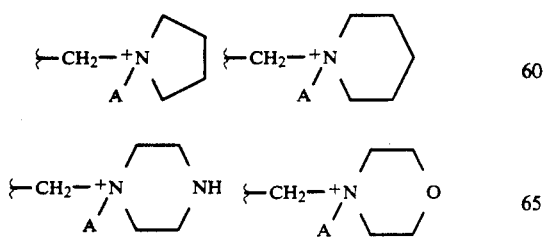

a pyridiniomethyl group;

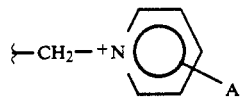

4-carbamoylpyridiniomethyl; or quinuclidiniomethyl which is unsubstituted or substituted by a carbamoyl group or by a group A; or (14') acetylaminomethyl, benzoylaminomethyl; or Ala-NH-CH$_2$—, Gly-NH-CH$_2$—, Val-NH-CH$_2$—, Pro-NH-CH$_2$—, Phe-NH-CH$_2$— wherein the terminal amino of Ala, Gly, Val, Pro, Phe is either free or acylated with a group selected from the group consisting of Ac, Cbz, Boc, succinyl and glutaryl; or Z-NH-CH$_2$ wherein Z represents Val-Pro, Ala-Ala or Ala-Pro and wherein the terminal amino group of Val and Ala is either free or acylated with a group selected from the group consisting of Ac, Cbz, Boc, succinyl and glutaryl;

or a pharmaceutically or veterinarily acceptable salt thereof.

3. The compound of claim 2, wherein R$^4$ is:
(12') —CH$_2$-Ala, —CH$_2$-Gly, or —CH$_2$-Val.

4. The compound of claim 1, having the formula (Ia")

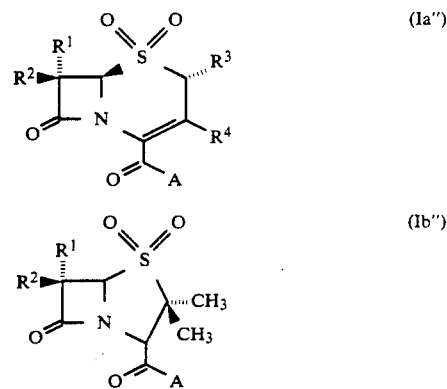

wherein:

A is selected from the group consisting of hydrogen, methyl, ethyl, tert-butyl, neo-pentyl, phenyl, benzyl, 1-phenylethyl, dimethylphenyl, diphenylmethyl, propenyl, phenylethinyl, cyclopentyl, 1-carboxycyclopentyl, diazomethyl, chloromethyl, hydroxymethyl, methoxymethyl, acetoxymethyl and pivaloyloxymethyl;

R$^1$ is selected from the group consisting of chloro, bromo, fluoro, methoxy, formamido, acetamido, trifluoroacetamido, methyl, ethyl, 1-(hydroxy)ethyl, 1-benzyloxycarbonyloxy)ethyl, (1-benzoyloxy)ethyl, 1-(phenylacetoxy)ethyl Ala-NH, Acetyl-Ala-NH, succinyl-Val-NH, L-Val-L-Pro-NH, succinyl-Lys-NH, Ala-Ala-Pro-NH, and acetyl-Ala-Ala-Pro-NH;

R$^2$ is hydrogen;

R$^3$ is hydrogen, methyl, or bromo;

R$^4$ is methyl, bromomethyl, acetoxymethyl hydroxymethyl, carbamoyloxymethyl, methoxymethyl, phenoxymethyl, aminomethyl, pyridiniomethyl or a group selected from:

(1) —CH$_2$OCONH—CH$_2$CO$_2$H;

(2) —CH$_2$OCONH—CH(R$^{VI}$)CO$_2$H wherein R$^{VI}$ is phenyl or C$_1$-C$_7$ straight or branched alkyl;
(3) —CH$_2$OC(O)CH$_2$CH$_2$CO$_2$H;
(4) —CH$_2$OC(O)—(p—C$_6$—H$_4$)—CO$_2$H or —CH$_2$OC(O)—(p—C$_6$H$_4$)—CO$_2$ $^t$C$_4$H$_9$;
(5) —CH$_2$O—C(O)—CH$_2$NH$_2$ or its N-Ac, N-Boc or N-CbZ derivative;
(6) —CH$_2$OC(O)—CH(NH$_2$)—CH$_3$ or its N-Ac, N-Boc or N-Cbz derivative;
(7) —CH$_2$OC(O)—CH(NH$_2$)—CH(CH$_3$)$_2$ or its N-Ac, N-Boc or N-Cbz derivative
(8) —CH$_2$OCOCH(CH$_3$)—NH—C(O)—(CH$_2$)$_3$—CO$_2$H;
(9)

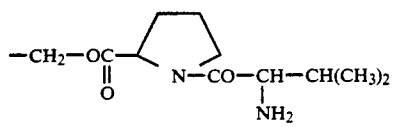

or its N-Ac, N-Boc or N-Cbz derivative;

(10)
—CH$_2$OCH$_2$—Ph or —CH$_2$O—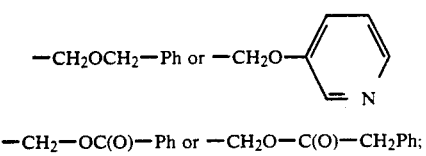

—CH$_2$—OC(O)—Ph or —CH$_2$O—C(O)—CH$_2$Ph; (11)

—CH$_2$SO$_2$CH$_3$ or —CH$_2$—S(O)Ph; (12)

(13)
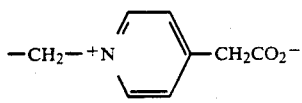

 (14)

(15) —CH$_2$NH—C(O)—CH(NH$_2$)—CH(CH$_3$)$_2$;
(16) —CH$_2$S-Het, wherein Het is a heterocyclic ring chosen from:

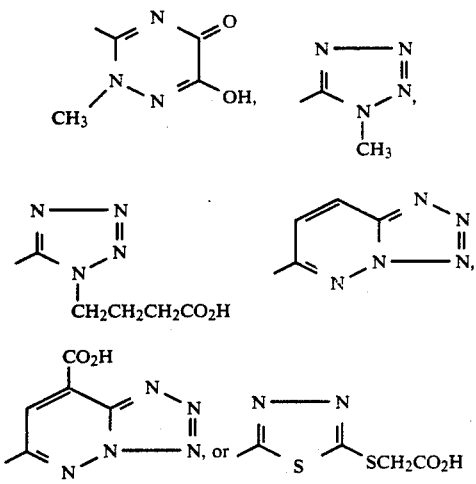

or a pharmaceutically or veterinarily acceptable salt thereof.

5. The compound of claim 3, said compound being chosen from
4-tert butylcarbonyl-(7α)-chloro-3-methyl-3-cephem 1,1-dioxide;
3-bromomethyl-4-tert-butylcarbonyl-(7α)-chloro-3-cephem 1,1-dioxide;
3-acetoxymethyl-4-tert-butylcarbonyl-(7α)-chloro-3-cephem 1,1-dioxide;
4-tert-butylcarbonyl-(7α)-chloro-3-methoxymethyl-3-cephem 1,1-dioxide;
4-tert-butylcarbonyl-(7α)-chloro-3-phenoxymethyl-3cephem 1,1-dioxide;
4-tert-butylcarbonyl-(7α)-chloro-3-pyridiniomethyl-3-cephem 1,1-dioxide chloride;
4-tert- butylcarbonyl-3-(2-carboxyethyl)carbonyloxymethyl-(7α)-chloro-3-cephem 1,1-dioxide;
3-benzoyloxymethyl-4-tert-butylcarbonyl-(7α)-chloro-3-cephem 1,1-dioxide;
4-tert-butylcarbonyl-3 -(p-carboxy)benzoyloxymethyl-(7α)-chloro-3-cephem 1,1-dioxide;
4-tert-butylcarbonyl-(7α)-chloro-3-phenylthiomethyl-3-cephem 1,1-dioxide;
4-tert-butylcarbonyl-(7α)-chloro-3-(3-pyridyl)oxymethyl-3-cephem 1,1-dioxide;
3-(aminomethylcarbonyl)oxymethyl-4-tert-butylcarbonyl-(7α)-chloro-3-cephem 1,1-dioxide;
3-tert-butylcarbonyl-(7α)-chloro-3-phenylsulphinylmethyl-3-cephem 1,1-dioxide;
3-acetoxymethyl-(7α)-chloro-4-ethylcarbonyl-3-cephem 1,1-dioxide;
3-acetoxymethyl-4-benzylcarbonyl-(7α)-chloro-3-cephem 1,1-dioxide;
3-acetoxymethyl-(7α)-chloro-4-neopentylcarbonyl-3-cephem 1,1-dioxide;
3-acetoxymethyl-(7α)-chloro-4-phenylcarbonyl-3-cephem 1,1-dioxide;
3-acetoxymethyl-(7α)-chloro-4-formyl-3-cephem 1,1-dioxide;
3-acetoxymethyl-4-acetoxymethylcarbonyl-(7α)-chloro-3-cephem 1,1-dioxide;
3-acetoxymethyl-(7α)-chloro-4- methoxymethylcarbonyl-3- cephem 1,1-dioxide;
3-acetoxymethyl-(7α)-chloro-4-chloromethylcarbonyl-3-cephem 1,1-dioxide;
3-acetoxymethyl-(7α)-chloro-4-diazomethylcarbonyl-3-cephem 1,1-dioxide;
3-acetoxymethyl-(7α)-chloro-4-hydroxymethylcarbonyl-3-cephem 1,1-dioxide;
3-acetoxymethyl-(7α)-chloro-4-phenoxymethylcarbonyl-3-cephem 1,1-dioxide;
4-tert-butylcarbonyl-(7α)-methoxy-3-methyl-3-cephem 1,1-dioxide;
3-acetoxymethyl-4-tert-butylcarbonyl-(7α)-methoxy-3-cephem 1,1-dioxide;
4-tert-butylcarbonyl-(7α)-methoxy-3-methoxymethyl-3-cephem 1,1-dioxide;
4-tert-butylcarbonyl-(7α)-methoxy-3-phenoxymethyl-3-cephem 1,1-dioxide;
4-tert-butylcarbonyl-(7α)-methoxy-3-pyridiniomethyl-3-cephem 1,1-dioxide chloride;
4-tert-butylcarbonyl-3-(2-carboxyethylcarbonyloxymethyl)-(7α)-methoxy-3-cephem 1,1-dioxide;
3-benzoyloxymethyl-4-tert-butylcarbonyl-(7α)-methoxy-3-cephem 1,1-dioxide;
4-tert-butylcarbonyl-3-(4-carboxybenzoyloxymethyl)-(7α)-methoxy-3-cephem 1,1-dioxide;
4-tert-butylcarbonyl-(7α)-methoxy-3-phenylsulphinylmethyl-3-cephem 1,1-dioxide;

3-(aminomethylcarbonyl)oxymethyl-4-tert-butylcarbonyl-(7α)-methoxy-3-cephem 1,1-dioxide;

3-(2-tert-butoxycarbonylamino-2-diphenylmethoxycarbonyl)-ethylthiomethyl-4-tert-butylcarbonyl-(7α)-methoxy-3-cephem 1,1-dioxide;

3-(2-tert-butoxycarbonylamino-2-carboxy)ethylthiomethyl-4-tert-butylcarbonyl-(7α)-methoxy-3-cephem 1,1-dioxide;

3-(2-amino-2-carboxy)ethylthiomethyl-4-tert-butylcarbonyl-(7α)-methoxy-3-cephem 1,1-dioxide;

3-acetoxymethyl-4-ethylcarbonyl-(7α)-methoxy-3-cephem 1,1-dioxide;

3-acetoxymethyl-(7α)-methoxy-4-neopentylcarbonyl-3-cephem 1,1-dioxide;

3-acetoxymethyl-(7α)-methoxy-4-phenylcarbonyl-3-cephem 1,1-dioxide;

3-acetoxymethyl-4-formyl-(7α)-methoxy-3-cephem 1,1-dioxide;

3-acetoxymethyl-(7α)-methoxy-4-methoxymethyl-3-cephem 1,1-dioxide;

3-acetoxymethyl-(7α)-methoxy-4-phenoxymethyl-3-cephem 1,1-dioxide;

3-acetoxymethyl-4-chloromethylcarbonyl-(7α)-methoxy-3-cephem 1,1-dioxide;

3acetoxymethyl-4-tert-butylcarbonyl-(7α)-fluoro-3-1,1-dioxide;

3-acetoxymethyl-4-tert-butylcarbonyl-(7α)-trifluoroacetamido-3-cephem 1,1-dioxide;

3-acetoxymethyl-4-tert-butylcarbonyl-(7α)-methyl-3-cephem 1,1-dioxide;

3-acetoxymethyl-4-tert-butylcarbonyl-(7α)-ethyl-3-cephem 1,1-dioxide;

3-acetoxymethyl-4 -tert-butylcarbonyl-(7α)-(1-hydroxyethyl)-3-cephem 1,1-dioxide;

3-acetoxymethyl-4-tert-butylcarbonyl-(7α)-1-(phenylacetoxy)ethyl-3-cephem 1,1-dioxide;

3-acetoxymethyl-(7α)-(2-acetylamino)propanoylamino-4-tert-butylcarbonyl-3-cephem 1,1-dioxide;

3-acetoxymethyl-4-tert-butylcarbonyl-(7α)-chloro-(2α)-methyl-3-cephem 1,1-dioxide; and 3-acetoxymethyl-4-tert-butylcarbonyl-(7α)-methoxy-(2α)-methyl-3-cephem 1,1-dioxide.

6. A pharmaceutical or veterinary composition containing a suitable carrier and/or diluent and, as an active principle, a 4-acylcephem sulphone of formula (Ia) or a pharmaceutically or veterinarily acceptable salt thereof:

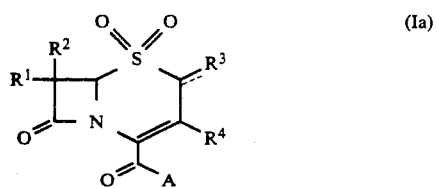

(Ia)

wherein:

A is a hydrogen atom or an organic radical selected from the group consisting of $C_1$-$C_{12}$ straight or branched alkyls; $C_2$-$C_{10}$ alkenyls; $C_2$-$C_{10}$ alkynyls; $C_6$-$C_{10}$ aryls; $C_3$-$C_8$ cycloalkyls; $C_5$-$C_8$ cycloalkenyls; $C_7$-$C_{22}$ aralkyls; $C_8$-$C_{12}$ aralkenyls; $C_8$-$C_{12}$ aralkynyls; $C_4$-$C_{20}$ (cycloalkyl)alkyls; 5- and 6-membered saturated and unsaturated heterocyclyl rings containing at least one heteroatom chosen from O, S and N; 5- and 6-membered saturated and unsaturated heterocyclyl rings fused to a 5- or a 6-membered heterocyclyl or to a $C_3$-$C_8$ cycloalkyl group; heterocycly-($C_{1-12}$)-alkyl, heterocycly-($C_2$-$C_{10}$)-alkenyl and heterocycly-($C_2$-$C_{10}$)-alkynyl wherein the heterocyclyl ring is selected from the group consisting of thiazolyl, triazolyl, thiadiazolyl, tetrazolyl, triazinyl, pyrrolyl, imidazolyl, furyl, thienyl, morpholinyl, pyranyl, pyridyl, pyrimidinyl, pyrazinyl, pyridazinyl and thiopyronyl;

wherein each of said organic radicals is unsubstituted or substituted by at least one substituent selected from the group consisting of halogen atoms; hydroxy; nitro; azido; diazo; —$NH_2$, —NHR' and —NR'R'', wherein R'and R'', which are the same or different, are $C_1$-$C_7$ straight or branched alkyl, phenyl or benzyl; —CHO; —SH; SR'; cyano; —$CO_2H$; —$CO_2R'$; —$SO_3H$; —C(O)R'; —C(O)$CF_3$; —$CONH_2$; —$CONHCH_3$; —CONH—$CH_2CO_2H$; —$OCONH_2$; —OC(O)R'; —OC(O)H; —C(O)R'; —OC(O)R'; —O—R'; —S—R'; —S(O)R'; —S(O)$_2$R'; —NHC(O)R'''; —NHC(O)OR''', wherein R''' is $C_1$-$C_7$ straight or branched alkyl, phenyl, benzyl, $CH_2CH_2CO_2H$ or $CH_2CH_2CH_2CO_2H$; —NH—$SO_2R'$; —NHC(=NH)$NH_2$; $C_1$-$C_4$ alkyl; $C_2$-$C_4$ alkenyl; $C_2$-$C_4$ alkynyl; $C_3$-$C_6$ cycloalkyl; and substituted methyl which is one member selected from the group consisting of chloromethyl, fluoromethyl, difluromethyl, trifluoromethyl, aminomethyl, azidomethyl, cyanomethyl, carboxymethyl, carbamoylmethyl, carbamoyloxymethyl, hydroxymethyl, $C_3$-$C_4$ alkoxycarbonylmethyl, and guanidinomethyl;

$R^1$ is:
 (1) chloro, fluoro, bromo or iodo;
 (2) a group A;
 (3) a group —O—A;
 (4) a group —S(O)$_n$A, wherein n is 0, 1 or 2;
 (5) a group —OC(O)A;
 (6) a group —O—$SO_2$A; or
 (7) a group —NHC(O)A or an acylamino group, —NH—Z, wherein Z is a mono, di- or tripeptide composed of D or L α-aminoacid(s) chosen from the group consisting of Ala, Gly, Val, Leu, Ile, Phe and Pro, wherein the terminal amino group of said amino acid is either free, or acylated by a group —C(O)R''' or a group —C(O)OR''';

$R^2$ is hydrogen or:
 (1) $C_1$-$C_4$ alkyl
 (2) $C_1$-$C_4$ alkanoyloxy; or
 (3) chloro, bromo or fluoro;

$R^3$ is hydrogen or:
 (1) $C_1$-$C_4$ alkyl;
 (2) $C_1$-$C_4$ alkoxy;
 (3) benzyl;
 (4) halo; or
 (5) a methylene group, =$CH_2$, or a group =$CHR^{IV}$, wherein $R^{IV}$ is $C_1$-$C_4$ alkyl, or phenyl, carboxy, or $C_1$-$C_4$ alkoxycarbonyl; and $R^4$ is:
 (1) a group A;
 (2) chloro or fluoro;
 (3) a group —O—A;
 (4) a group —S(O)$_n$A;
 (5) a group —C(O)A, —C(O)OA or —$CO_2H$;
 (6) a group —$CH_2$—O—A;
 (7) a group —$CH_2S(O)_n$A;
 (8) a group —$CH_2OC(O)$A or —$CH_2$—O—Z;

(9) a group —CH₂SC(O)A;
(10) a group —CH₂—N(A)A' wherein A', being the same or different as A, is a group as defined for A; or A and A' taken together with the nitrogen atom to which they are attached represent a heterocyclic ring selected from the aforementioned group;
(11) a group

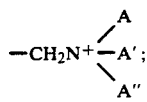

wherein A", being the same or different or A or A', is as defined for A; or A is C₁-C₁₂ alkyl and A' and A" together with the nitrogen atom to which they are attached represent a heterocyclic ring selected from the group consisting of piperidine, pyrrolidino, piperazine and morpholino; or A, A' and A" together with the nitrogen atom to which they are attached represent pyridinio of the formula

(12) a group —CH₂NH—C(O)A or —CH₂—N-H—Z.

7. A method for inhibiting the activity of HLE in a mammal, comprising administering to said mammal an effective amount of a 4-acylcephem sulphone of formula (Ia) or a pharmaceutically or veterinarily acceptable salt thereof:

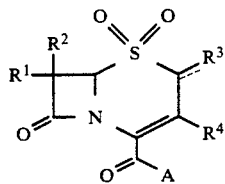

wherein:

A is a hydrogen atom or an organic radical selected from the group consisting of C₁-C₁₂ straight or branched alkyls; C₂-C₁₀ alkenyls; C₂-C₁₀ alkynyls; C₆-C₁₀ aryls; C₃-C₈ cycloalkyls; C₅-C₈ cycloalkenyls; C₇-C₂₂ aralkyls; C₈-C₁₂ aralkenyls; C₈-C₁₂ aralkynyls; C₄-C₂₀ (cycloalkyl)alkyls; 5- and 6-membered saturated and unsaturated heterocyclyl rings containing at least one heteroatom chosen from O, S and N; 5- and 6-membered saturated and unsaturated heterocyclyl rings fused to a 5- or 6-membered heterocyclyl or to a C₃-C₈ cycloalkyl group; heterocycly-(C₁₋₁₂)-alkyl, heterocycly-(C₂-C₁₀)-alkenyl and heterocycly-(C₂-C₁₀)-alkynyl wherein the heterocyclyl ring is selected from the group consisting of thiazolyl, triazolyl, thiadiazolyl, tetrazolyl, triazinyl, pyrrolyl, imidazolyl, furyl, thienyl, morpholinyl, pyranyl, pyridyl, pyrimidinyl, pyrazinyl, pyridazinyl and thiopyronyl;

wherein each of said organic radicals is unsubstituted or substituted by at least one substituent selected from the group consisting of halogen atoms; hydroxy; nitro; azido; diazo; —NH₂, —NHR' and —NR'R", wherein R'and R", which are the same or different, are C₁-C₇ straight or branched alkyl, phenyl or benzyl; —CHO; —SH; R'; cyano; —CO₂H; —CO₂R'; —SO₃H; —C(O)R'; —C(O)CF₃; —CONH₂; —CONHCH₃; —CONH—CH₂CO₂H; —OCONH₂; —OC(O)R'; —OC(O)H; —C(O)R'; —OC(O)R'; —O—R'; —S—R'; —S(O)R'; —S(O)₂R'; —NHC(O)R'''; —NHC(O)OR''', wherein R''' is C₁-C₇ straight or branched alkyl, phenyl, benzyl, CH₂CH₂CO₂H or CH₂CH₂CH₂CO₂H; —NH—SO₂R'; —NHC(=NH)NH₂; C₁-C₄ alkyl; C₂-C₄ alkenyl; C₂-C₄ alkynyl; C₃-C₆ cycloalkyl; and substituted methyl which is one member selected from the group consisting of chloromethyl, fluoromethyl, difluromethyl, trifluoromethyl, aminomethyl, azidomethyl, cyanomethyl, carboxymethyl, carbamoylmethyl, carbamoyloxymethyl, hydroxymethyl, C₃-C₄ alkoxycarbonylmethyl, and guanidinomethyl;

R¹ is:
(1) chloro, fluoro, bromo or iodo;
(2) a group A;
(3) a group —O—A;
(4) a group —S(O)ₙA, wherein n is 0, 1 or 2;
(5) a group —OC(O)A;
(6) a group —O—SO₂A; or
(7) a group —NHC(O)A or an acylamino group, —NH—Z, wherein Z is a mono, di- or tripeptide composed of D or L α-aminoacid(s) chosen from the group consisting of Ala, Gly, Val, Leu, Ile, Phe and Pro, wherein the terminal amino group of said amino acid is either free, or acylated by a group —C(O)R''' or a group —C(O)OR''';

R² is hydrogen or:
(1) C₁-C₄ alkyl
(2) C₁-C₄ alkanoyloxy; or
(3) chloro, bromo or fluoro;

R³ is hydrogen or:
(1) C₁-C₄ alkyl;
(2) C₁-C₄ alkoxy;
(3) benzyl;
(4) halo; or
(5) a methylene group, =CH₂, or a group =CHR^{IV}, wherein R^{IV} is C₁-C₄ alkyl, or phenyl, carboxy, or C₁-C₄ alkoxycarbonyl; and R⁴ is:
(1) a group A;
(2) chloro or fluoro;
(3) a group —O—A;
(4) a group —S(O)ₙA;
(5) a group —C(O)A, —C(O)OA or —CO₂H;
(6) a group —CH₂—O—A;
(7) a group —CH₂S(O)ₙA;
(8) a group —CH₂OC(O)A or —CH₂—O—Z;
(9) a group —CH₂SC(O)A;
(10) a group —CH₂—N(A)A' wherein A', being the same or different as A, is a group as defined for A; or A and A' taken together with the nitrogen atom to which they are attached represent a heterocyclic ring selected from the aforementioned group;
(11) a group

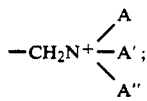

wherein A", being the same or different or A or A', is as defined for A; or A is $C_1$-$C_{12}$ alkyl and A' and A" together with the nitrogen atom to which they are attached represent a heterocyclic ring selected from the group consisting of piperidine, pyrrolidino, piperazine and morpholino; or A, A' and A" together with the nitrogen atom to which they are attached represent pyridinio of the formula

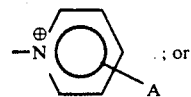

(12) a group —CH$_2$NH—C(O)A or —CH$_2$—NH—Z.

8. The treatment of claim 7, wherein said mammal is a human.

* * * * *